(12) United States Patent
Ugrai et al.

(10) Patent No.: US 11,672,804 B1
(45) Date of Patent: Jun. 13, 2023

(54) PHARMACEUTICAL COMPOSITION CONTAINING PALBOCICLIB AND LETROZOLE

(71) Applicant: EGIS Gyógyszergyár Zrt., Budapest (HU)

(72) Inventors: László Ugrai, Budapest (HU); Gyula Lukács, Budapest (HU)

(73) Assignee: EGIS Gyógyszergyár Zrt., Budapest (HU)

( * ) Notice: Subject to any disclaimer, the term of this patent is extended or adjusted under 35 U.S.C. 154(b) by 0 days.

(21) Appl. No.: 17/891,566

(22) Filed: Aug. 19, 2022

(51) Int. Cl.
| | | |
|---|---|---|
| *A61K 31/519* | (2006.01) | |
| *A61K 31/4196* | (2006.01) | |
| *A61K 9/20* | (2006.01) | |
| *A61K 9/00* | (2006.01) | |

(52) U.S. Cl.
CPC .......... *A61K 31/519* (2013.01); *A61K 9/0056* (2013.01); *A61K 9/20* (2013.01); *A61K 31/4196* (2013.01); *C07B 2200/13* (2013.01)

(58) Field of Classification Search
CPC .............. A61K 31/519; A61K 31/4196; A61K 9/0056; A61K 9/20; C07B 2200/13
See application file for complete search history.

(56) References Cited

U.S. PATENT DOCUMENTS

| | | | | |
|---|---|---|---|---|
| 6,936,612 B2 * | 8/2005 | Barvian | .................. | A61P 13/12 514/264.11 |
| 7,208,489 B2 * | 4/2007 | Barvian | .................. | A61P 31/00 514/264.11 |
| 7,456,168 B2 * | 11/2008 | Barvian | .................. | A61P 43/00 514/264.11 |

* cited by examiner

*Primary Examiner* — Erich A Leeser
(74) *Attorney, Agent, or Firm* — Millen White Zelano and Branigan, PC; Csaba Henter

(57) ABSTRACT

A pharmaceutical composition containing palbociclib tosylate and letrozole, in which palbociclib tosylate and letrozole are in one dosage unit, and the particles of the active ingredient palbociclib tosylate and letrozole are not separated from each other, and the production of the pharmaceutical preparation, the granule containing palbociclib tosylate and letrozole, the use of the pharmaceutical preparation and special blister packaging that facilitates the use of a specific dosage regimen.

20 Claims, 7 Drawing Sheets

PHARMACEUTICAL COMPOSITION CONTAINING PALBOCICLIB AND LETROZOLE

THE SUBJECT OF THE INVENTION

The present invention relates to a pharmaceutical composition comprising palbociclib tosylate and letrozole, wherein palbociclib tosylate and letrozole are in a unit dose and the active ingredient particles, palbociclib tosylate and letrozole are not separated. The invention further relates to the preparation of the pharmaceutical composition, to the granules containing palbociclib tosylate and letrozole, to the use of the pharmaceutical composition and to a special blister pack which facilitates the use of a specific dosage regimen.

TECHNICAL BACKGROUND

Palbociclib is an anticancer medicine used to treat breast cancer if the cancer is locally advanced (spread nearby) or metastatic (spread to other parts of the body). Palbociclibe is used when there are receptors (targets) for certain hormones on the surface of cancer cells (HR-positive) and they do not produce abnormally high levels of a receptor called HER2 (HER [human epidermal growth factor] negative). Palbociclib is used in combination with an aromatase inhibitor (a hormonal anticancer medicine) or fulvestrant (another hormonal anticancer medicine) in patients who have been treated with a previous hormonal medicine. Thus, palbocilib is used in combination in the current treatment. It is widely used in combination with letrozole as an aromatase inhibitor, which has been used since 1996 to treat hormonally responsive breast cancer after surgery. Palbociclib of the formula

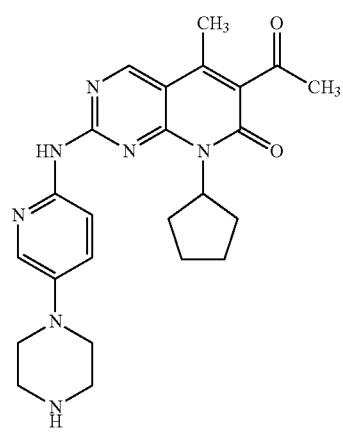 [SMILES: CC(=O)c1c(C)c2cnc(Nc3ccc(N4CCNCC4)cn3)nc2n(C2CCCC2)c1=O]

(I) and its pharmaceutically acceptable salts are described in descriptions of WO 2003/062236 and U.S. Pat. Nos. 6,936,612, 7,208,489 and 7,456,168 patents and patent applications. WO17072543 A1 describes additional salts of palbociclib which appear to be pharmaceutically acceptable. Letrozole of formula

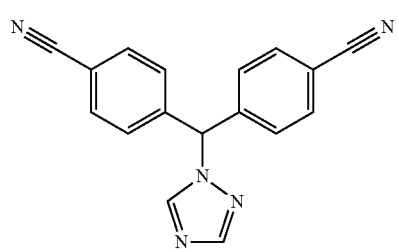 [SMILES: N#Cc1ccc(C(c2ccc(C#N)cc2)n2cncn2)cc1]

(II) is described in EP236940 B1. Palbociclib and letrozole are administered to those in need in separated dosage forms according to the state of the art. However, the solubility of palbociclib is strongly pH dependent. Since the palbociclib base is soluble only in a strongly acidic medium, on an empty stomach, it can be classified as sparingly soluble compound. Thus, it has become necessary to prepare a composition that can be used regardless of the time of a meal, or even in a group of patients who are taking a proton pump paralyzer, for example, which prevents the development of strongly acidic stomach contents. Under these conditions, the solubility of palbociclib is in the very slight soluble category which makes it impossible to use palbociclib in the absence of adequate dissolution. According to EP3302565 B1, this problem can be solved by incorporating an acidic excipient into the palbociclib-containing composition, which is believed to provide an acidic microenvironment for the palbociclib base during dissolution. Thus, a composition is obtained from which it dissolves well even at higher pH values between 4.5 and 5.5. In the case of the compound with a similar chemical structure, ribociclib, the dissolution was converted to a salt formed by salt formation, namely succinic acid, as described in WO16166703 A1, so that it showed a suitable dissolution even at pH 4.5. As both ribociclibe and palbociclibe have long been used in combination with letrozole, there has been a need to use the two active substances, ribociclibe or palbociclibet, in combination with letrozole.

The combination products have an important advantage over mono products given in combination, that it is sure that both active substances are taken in the same time by the patient, and the two active substances enter the body at the same time, resulting blood levels during the absorption of the two active substances in safe values as it was designed and tested during authorization. The distributor of ribociclib has already marketed a combination dosage form containing the two active ingredients in separate tablets (KISQALII FEMARA CO-PACK (COPACKAGED)). While such KITs have the advantage of at least ensuring that both tablets are available, they do not ensure that the patient takes both or that they take them on time, together, or immediately after each other. Despite the obvious need for a combination preparation, the ribociclib letrozole combination was implemented not as a safer, fixed-dose combination preparation, but as a pharmaceutical co-pack containing the two active ingredients in separate dosage forms. However, the combination of palbociclib-letrozole has not been marketed even in the form of KIT. Thus, it is apparent that in order to increase patient safety, there is a need for a fixed dose combination of letrozole and palbociclib, which is preferably dissolved in the stomach at pH 4.5-5.5, independently of a meal, even with a proton pump inhibitor, and allows appropriate absorption of the active ingredients, palbociclib and letrozole.

BRIEF SUMMARY OF THE INVENTION

The present invention provides a pharmaceutical composition comprising the 4-toluenesulfonic acid salt of Palbociclib and letrozole, preferably a fix dose combination composition. In particular, the pharmaceutical composition of the present invention is a fixed dose combination composition comprising a salt modification of palbocilib tosylate (1:1) and letrozol. More preferably, the fixed dose oral combination composition comprises besides letrozole and 4-toluenesulfonic acid (1:1) salt of palbociclib having characteristic X-ray powder diffraction peaks of the as follows: 2θ (±0.2° 2θ): 5.18; 10.25; 13.45; 16.08; 21.56.

In particular, the invention may be characterized as a pharmaceutical composition in which the two active ingredients, the tosylate salt of palbociclib, preferably 4-toluenesulfonic acid (1:1) salt of palbociclib having characteristic X-ray powder diffraction peaks listed in paragraph above and letrozole are not separated, not isolated from each other. So, the active ingredients are homogenized in the composition. This can also be expressed as, for example, during granulation, both active ingredients are included in the mixture to be granulated, they are preferably granulated together, even more preferably they are dry granulated together, most preferably they are compacted together. But we can also proceed by homogenizing the mixture of palbocilib toluenesulfonic acid salt and letrozole with excipients and pressing it into a tablet or filling it in a capsule. Therefore, the preferred embodiment of our invention can be a tablet, capsule, powder mixture, or granulates. Most preferably granules, tablet or capsule. More specifically, the pharmaceutical preparation according to the present invention is a fixed-dose combination preparation in which the crystalline form of palbociclib tosylate (1:1) salt and letrozole are present, and wherein the 4-toluenesulfonic acid salt of palbociclib is not separated (isolated) from letrozole. More preferably, a fixed-dose oral combination pharmaceutical composition in which the positions of the characteristic X-ray powder diffraction peaks of palbociclib 4-toluenesulfonic acid (1:1) salt are as follows: Cu Kα (1.1541874 Å) (±0.2° 2θ): 5.18; 10.25; 13.45; 16.08; 21.56 and there is letrozole, in which composition letrozole is not separated (isolated) from palbociclib 4-toluenesulfonic acid (1:1) salt.

More particularly, the present invention relates to tablets or capsules prepared using granules, preferably dry granules, more preferably compacts containing palbocilib tosylate (1:1) salt and letrozole, and in which granules the 4-toluenesulfonic acid salt of palbociclib is not isolated from letrozole. But we can also define that in the composition, the particles of palbociclib tosylate and letrozole form a mixture optionally with other excipients, in which there is no significant difference between the parts of the mixture in composition. Thus, both in the formulation or in the granules containing both active ingredients, the particles of the active ingredients and the particles of the excipient are randomly, evenly arranged. Such a mixture is a pharmaceutically homogeneous mixture If the mixtures are considered homogenous in which the particles of active ingredients and excipients are located randomly, it can be said that our invention relates a composition in which palbociclib 4-toluenesulfonic acid (1:1) salt and letrozole form a homogeneous mixture with additional excipients.

The physical separation of the active ingredients is generally carried out by coating the particles of one or the other active ingredient or both, placing the active ingredients in different phases, layers or coating layers, optionally including a separating layer between the active ingredient layers. In such compositions, the distribution is typically not homogeneous because the composition is completely different within the different but separated phases. If the coated particles or granules are mixed in one phase, the location of the coated particles may be uniform in the system, but the coating divides phases, which thus do not contact each other and form separate phases.

Surprisingly, in the composition of the present invention comprising palbociclib tosylate salt and letrozole it is not necessary the separation of the two active ingredients from each other.

So, surprisingly, we found that if the 1:1 molar ratio of palbociclib 4-toluenesulphonic acid, letrozol and other excipients, preferably a filler and, optionally, as additional excipients, a binder, a disintegrant, a glidant and a lubricant, are mixed, homogenised and subjected to dry granulation, preferably compacted, and the resulting granules, if appropriate mixed with additional excipients to provide the external phase, are filled into capsules or pressed into tablets, resulting in a formulation which is stable for at least 6 months as described in example 5, and whose dissolution at both highly acidic and less acidic pH 4,5-5,5 corresponds to the dissolution profile observed in the co-dissolution of the corresponding mono-formulations, i.e. the dissolution data of the combination formulation when statistically analysed are equivalent to the dissolution data observed in the co-dissolution study of the mono-formulations with respect to the dissolution of both letrozole and palbociclib. This means that the preparation according to our invention can be used to replace the parallel administration of mono preparations.

DETAILED DESCRIPTION OF THE INVENTION

The present invention therefore provides a pharmaceutical composition comprising the 4-toluenesulfonic acid salt of Palbociclib and letrozole. The composition comprises preferably a of palbocilib tosylate (1:1) form. More preferably, the pharmaceutical composition comprises a polymorphic form of the 4-toluenesulfonic acid (1:1) salt of palbociclib having characteristic X-ray powder diffraction peaks: Cu Kα (1.1541874 Å) (±0.2° 2θ): 5.18; 10.25; 13.45; 16.08; 21.56. A preferred embodiment of the pharmaceutical composition according to the invention comprises 10 to 50% by weight, preferably 20 to 40% by weight, most preferably 25 to 35% by weight of palbocyclib tosylate salt, 0.10 to 1% by weight, preferably 0.20 to 0.80% by weight, more preferably contains 0.35-0.80% by weight of letrozole. Most preferably, the amount of palbocilib tosylate based on palbociclib base in the pharmaceutical composition of the present invention is 75 mg, 100 mg or 125 mg, and the amount of letrozole is 2.5 mg. The pharmaceutical composition according to the invention preferably contains, in addition to the active ingredients, at least one further excipient, preferably a filler, a binder, a disintegrant, a lubricant and/or a glidant, or any mixture thereof. The present invention further provides a granulate comprising palbociclib tosylate and letrozole, which can be encapsulated or tableted to form a tablet or capsule of the present invention.

The meaning of fixed dose combination formulation according to the present invention is a composition in which the ratio of the two active ingredients, palbociclib tosilate and letrozole is a specified value. Such a fixed dose combination granule is a granule according to the invention which has a substantially equal weight ratio of palbocilib tosylate to letrozole in every granule, taking into account the measurement limits. Most preferably, the palbocilib tosylate rate to letrozole in the granules of the present invention calculated as palbociclib base is 75:2.5, 100:2.5 or 125:2.5. However, such fixed dose combination compositions may be formulated in unit dosage form.

These are unit doses in which not only the ratio of palbociclib to letrozole is determined, but also the amount of active ingredients present in the formulation. Examples of such preparations are tablets, capsules, which contain the same amount of palbociclib tosylate and letrozole within certain error limits. Most preferably, such unit doses are capsules or tablets in which the amount of palbociclib tosylate based on palbociclib base is 75 mg, 100 mg or 125 mg and the amount of letrozole is 2.5 mg.

The oral fixed dose compositions of the present invention, including fixed dose unit doses, are preferably used in a dosage regimen for the treatment of cancer in which letrozole monotherapy is administered for 7 days after 21 fixed dose combination compositions. Monotherapy is defined as a treatment which is carried out with a so-called mono-composition containing only one active substance in present case comprising letrozol.

This method of treatment according to the present invention can be carried out by using a drug kit (Kit), a special blister or secondary packaging (e.g. wallet packaging) in which or on which the combination unit doses and mono unit doses are arranged in the order of the planned dosage sequence.

The tablet or capsule according to the invention optionally contains additional excipients in addition to the granules as an external phase.

According to a highly preferred embodiment of the invention, the pharmaceutical composition according to the invention comprise besides the active ingredients namely the 4-toluene sulfuric acid salt of palbociclib and letrosol further comprises 50-90% by weight, preferably 55-85% by weight, more preferably 60-80% by weight, most preferably 60-70% by weight of filler and, optionally, further excipients.

The composition according to the invention may comprise as further excipients optionally, in an amount of 1 to 10% by weight, preferably 1 to 5% by weight, most preferably 1 to 2% by weight of binder, 1 to 15% by weight, preferably 2 to 12% by weight, most preferably 2 to 8% by weight, more preferably 5-8% by weight of a disintegrant and optionally 0.1-2% by weight, preferably 0.2-1.5% by weight, 0.5-1.0% by weight of glidant and 0.1-3% by weight, preferably 0.5-3.0% by weight, most preferably 1.0-2.5% by weight of lubricant. In a most preferred embodiment of the present invention the composition does not contain a binder.

The pharmaceutical composition of the present invention can comprise
- as filler any organic or inorganic filler compatible with palbociclib and letrozole, as organic filler preferably sugar alcohols, as sugar alcohol preferably mannitol, isomalt, lactitol, maltitol or sorbitol, as polymeric filler preferably cellulose derivatives, more preferably microcrystalline cellulose or silanized microcrystalline cellulose such as Prosolv HD 90,
- optionally, any binder compatible with palbocyclib and letrozole, such as polyvinyl pyrrolidone, starch, dextran, cellulose derivatives, such as hydroxypropyl methylcellulose,
- optionally, it may comprise as a disintegrant any disintegrant compatible with palbociclib and letrozole, preferably a crosslinked polyvinyl pyrrolidone type disintegrant, crospovidone, preferably Poliplasdone XL 10, sodium carboxyl, starch derivatives, most preferably Sodium starch glycolate type A, or carboxymethylcellulose salts, preferably croscaramellose sodium,
- optionally, the lubricant may be any lubricant compatible with palbociclib and letrozole, preferably stearic acid, stearic acid salts or derivatives, preferably magnesium stearate or sodium stearyl fumarate, most preferably magnesium stearate,
- optionally, any glidant compatible with palbociclib and letrozole, preferably talc, or colloidal silica, more preferably anhydrous colloidal silica, such as Aerosil 200, or a hydrophobic colloidal silica, such as Aerosil R 972.

The most preferred embodiment of the invention is an amount of palbociclib tosylate (1:1) corresponding to 75 mg, 100 mg or 125 mg of palbociclib base and 2.5 mg of letrozole, and 50-90% by weight, preferably 55-85% by weight, more preferably 60-80% by weight most preferably 60-70% by weight of microcrystalline cellulose, 2-10% by weight, preferably 2-8% by weight of crospovidone, 0.2-2.0% by weight, preferably 0.5-1.5% by weight of colloidal silicon dioxide and 0.1%-3.0% by weight, preferably 0.5-3.0% by weight, most preferably 1.0-2.5% by weight of magnesium stearate.

In a highly preferred embodiment of the composition of the present invention, the composition is a capsule or tablet. In a most preferred embodiment of the invention, the tablet is coated. The coating does not affect the dissolution of the tablet of the present invention. In the case of the present invention, the role of the coating is to improve its aesthetic appearance and to make the colorants used in the coating distinguish the tablet from other similar tablets.

Any tablet coating system used in the pharmaceutical industry that is compatible with palbociclib and letrozole can be used which is readily soluble in a wide pH range, preferably in aqueous media below pH 8, thus the coating does not inhibit the wetting of the tablet in the stomach. Such systems generally comprise film-forming, coating materials and, optionally, additional auxiliaries such as plasticizers, glidants and colorants. The tablets exemplified in our present application are coated with a Vivacoat PA-3P-468 coating suspension.

Our research was based on the preparation of a tablet containing palbocilib base as well as succinic acid as described in EP3302565 and further comprised letrozol also in the inner phase of the tablet. This formulation was described in Comparative Example 2, batch No. PLE0400620). From the PLE0400620 formulation described in the comparative example, the dissolution of palbociclib and letrozole in different pH buffers was also tested. The surprising result was that the dissolution of palbociclib in the pH 5.5 buffer solution from palbociclib, succinic acid and letrozole was similar to that of the corresponding mono-formulation, IBRANCE (FIG. 1), but in the case we compared the dissolution of letrozole to that of with a profile prepared by simultaneously dissolving one IBRANCE tablet and one FEMARA SNT20 tablet in one run, from one pot, it was found that the release of letrozole from the fix dose combination composition was inhibited (FIG. 2).

The difference in dissolution is significant and unfavorable because, based on the dissolutions, the dissolution of the resulting formulation cannot be considered statistically equivalent to the dissolution observed when co-administered. It follows that its absorption and bioavailability may differ from the combination dose. In such cases, the authorities consider whether the compliance with the medicine's effectiveness and pharmacovigilance requirements requires complete clinical trial. Complete clinical trial involves very significant costs and if the product is not bioequivalent, if it is authorized at all, the combination product will not be used as a replacement therapy of the prior art combination treatment. This is of great importance in this case, because palbociclib and letrozole are administered in the currently accepted treatment regimen in combination with 75 mg, 100 mg or 125 mg of palbociclib base and 2.5 mg of letrozole once daily for 21 days, then the combination therapy is followed by letrozole monotherapy 2.5 mg daily for 7 days. This 28-day treatment cycle is repeated several times as needed. Occasionally, the combination will be administered with different amounts of palbocilib as discretion of the physician. Thus, according to the prior art, 2 tablets a day, one tablet containing palbocilib and one letrozole should be taken for 21 days, followed by 1 tablet for 7 days. In this case, there is a very high risk that the patient will be mistaken during the shift days of the cycle, where the combination should be switched from monotherapy to vice versa.

Furthermore, it is very important that palbociclib dissolves well not only at low pH in the fasting state, but also in the pH range of 4.5-5.5. In the patent application no.: EP3302565 the authors disclose the inclusion of an acidic excipient in a tablet containing palbociclib, which provides an acidic microenvironment to improve the dissolution of palbociclib particles in the weakly acidic medium when the tablet dissolves. It is emphasized that three acids are suitable for improving the solubility of palbociclib in terms of dissolution and stability, malic acid, tartaric acid and succinic acid. The application also investigated the effects of a number of acids, such as citric acid, fumaric acid, benzenesulfonic acid, maleic acid, benzoic acid and p-toluenesulfonic acid. These acids did not significantly improve dissolution. Tartaric acid, succinic acid and malic acid are aliphatic dicarboxylic acids with very similar pKa values. Thus, it is highly probable to the person skilled in the art that if succinic acid slows down the dissolution of letrozole, tartaric acid and malic acid may have a similar effect, so that the addition of both active ingredients from the combination formulation is not adequate. Surprisingly, it has been found that when para-toluenesulfonic acid is present as a palbociclib salt and not in the form of an acid in addition to the base, as described in EP3302565, the dissolution of palbociclib from the tablet is the same as that of the IBRANCE tablet and the dissolution of letrozole from the product of the present invention is the same as the dissolution of letrozole dissolved simultaneously in one run in a single-cup IBRANCE tablet and one FEMARA SNT20 tablet. This means that the fact that para-toluenesulphonic acid is used as a salt former dissolves 73.6% of palbociclib in the buffer pH 5.5 in the first 30 minutes, while under the same conditions, if it is present as an acid, then only 49% dissolution of palbociclib according to the first figure of EP3302565. Moreover, the figure shows that the total dissolution after 180 minutes is only 59%. It is already surprising that the use of para-toluenesulfonic acid as a salt in a stoichiometric ratio of 1:1 causes much greater dissolution in as short time as 30 minutes and completes the dissolution. It allows palbociclib to dissolve completely within 60 minutes in pH 5.5 buffer. It has also been surprisingly found that the palbociclib 4-toluenesulphonic acid (1:1) salt described in WO17072543 A1 remains stable in the pharmaceutical composition in the presence of letrozole.

Indeed, although WO17072543 A1 assumes that the stability of the salt is sufficient to be stable in a formulation, this is not demonstrated by actual formulation experiments. The fact that a salt form is stable alone, does not mean that it remains table in the formulation.

Because if the stable salt form dissociates in the composition due to one of the components of the composition, and then one of the resulting acid and base components reacts with either the excipient or possibly the other drug molecule, the equilibrium is shifted, which can cause intense degradation.

It is known that the interaction of salts can take place even in the solid phase, in the presence of relatively low moisture content. The tosylate salt of palbociclib is a strong acid salt of a weak base that can dissociate and release para-toluenesulfonic acid upon exposure to moisture.

Since para-toluenesulphonic acid degrades not only palbocyclibe but also letrozole, according to our experiments, it was expected, that the dissolution of palbociclib 4-toluenesulfonic acid salt result enough amount of 4-toluenesulfonic acid which capable of to start the degradation of letrozole, due to the high concentration of palbociclib tosylate, around 30-40 weight %, moreover, its ratio is several times that of letrozole in the composition according to the present invention. One skilled in the art would expect that such tablets should be exposed to air humidity or excipients, e.g. introduced with microcrystalline cellulose approx. to 3-3.5% moisture, letrozole and palbociclib begin to degrade in the presence of para-toluenesulfonic acid released from the salt. According to our measurements (Example 5.2), letrozole undergoes very significant degradation in the presence of para-toluenesulfonic acid. Surprisingly, however, the formulation is stable over the long term, despite that palbociclib is present in the form of the p-toluenesulfonate salt.

The composition of the present invention can be prepared by mixing the 4-toluenesulfonic acid salt of palbociclib, letrozole, preferably with a filler, optionally additional excipients such as a binder, a disintegrant and a lubricant or any mixture thereof, and then homogenizing the resulting mixture, then granulating the resulting homogenate by a dry granulation process, preferably compaction, optionally mixing additional excipients, preferably an additional lubricant, and optionally an additional disintegrant, as an external phase, and then encapsulating or tableting the resulting mixture, and optionally the tablet thus obtained is coated.

The used palbocycl tosylate salt is preferably 4-toluenesulfonic acid (1:1). More preferably, the polymorphic form of this salt has characteristic X-ray powder diffraction peaks: Cu Kα (1.1541874 Å) (±0.2° 2θ): 5.18; 10.25; 13.45; 16.08; 21.56.

In the process for the preparation of the composition according to the present invention, 10 to 50% by weight of the composition, preferably 20 to 40% by weight, most preferably 25 to 35% by weight of palbocyclib tosylate salt, and 0.10 to 1% by weight, preferably 0.20 to 0.80% by weight, more preferably 0.35-0.80% by weight of letrozole are used.

The exact content of the unit dose of the combination preparation per active ingredient can be varied as required within the above limits. Mono-drug combinations used in current treatment protocols indicate that palbociclib 75 mg, 100 mg, or 125 mg base is co-administered with 2.5 mg letrozole. Thus, in a most preferred embodiment of the invention, combination dosage units, tablets or capsules are prepared in which the amount of palbociclib tosylate used is 75 mg, 100 mg or 125 mg, based on palbocyclib base, and the amount of letrozole is 2.5 mg. The standard deviation of the active ingredient content of the compositions is determined for each dosage unit, e.g. between capsules and tablets. Thus, the true average active ingredient content of the compositions according to the invention may differ from the nominal content by ±10%, preferably by ±5%. For example, the average active ingredient content of tablets with a nominal potency of 75 mg calculated on a palbociclib base is between 67.5% and 82.5% calculated on a palbociclib base. The average active ingredient content can be measured by measuring the total active ingredient content of 100 tablets and expressing the amount obtained in mg and then dividing by 100.

In the process for preparing the composition according to the invention, 50 to 90% by weight, preferably 55 to 85% by weight, more preferably 60 to 80% by weight, most preferably 60 to 70% by weight of filler and optionally further excipients are used. As further excipient 1 to 10% by weight, preferably 2 to 5% by weight % by weight, most preferably 1-2% by weight of binder, 1 to 15% by weight, preferably 2 to 10% by weight %, more preferably 2 to 8% by weight %, most preferably 5-8% by weight of disintegrant and optionally 0.1-2% by weight, preferably 0.2-1.5% by weight, 0.5-1.0% by weight of glidant and 0.1-3% by weight, preferably 0.5-3.0% by weight, most preferably 1.0-2.5% by weight of lubricant are used.

The individual excipients, such as fillers, disintegrants, lubricants and glidants, can also be used to prepare granules, but some of them are used in the preparation of granules and others are used in admixture with the outer phase. In a highly preferred embodiment of the invention, for example, lubricants, glidants and disintegrants are present in both the granule and the outer phase.

In the process for preparing the composition of the invention
- as filler any organic or inorganic filler compatible with palbociclib and letrozole, as organic filler preferably sugar alcohols, as sugar alcohol preferably mannitol, isomalt, lactitol, maltitol or sorbitol, as polymeric filler preferably cellulose derivatives, more preferably microcrystalline cellulose or silanized microcrystalline cellulose such as Prosolv HD 90,
- optionally, as binder, any binder compatible with palbocyclib and letrozole, such as polyvinyl pyrrolidone, starch, dextran, cellulose derivatives, such as hydroxypropyl methylcellulose,
- optionally, as a disintegrant any disintegrant compatible with palbociclib and letrozole, preferably a crosslinked polyvinyl pyrrolidone type disintegrant, crospovidone, preferably Poliplasdone XL 10, sodium carboxyl, starch derivatives, most preferably Sodium starch glycolate type A, or carboxymethylcellulose salts, preferably croscaramellose sodium,
- optionally, as lubricant any lubricant compatible with palbociclib and letrozole, preferably stearic acid, stearic acid salts or derivatives, preferably magnesium stearate or sodium stearyl fumarate, most preferably magnesium stearate,
- optionally, as glidant any glidant compatible with palbociclib and letrozole, preferably talc, or colloidal silica, more preferably anhydrous colloidal silica, such as Aerosil 200, or a hydrophobic colloidal silica, such as Aerosil R 972 can be used.

In the compositions according to present invention optionally, several types of fillers, binders, disintegrants, lubricants and glidants may be used together in the composition of the present invention, either in both phases or, for example, in the inner phase, in the granules, other fillers, binders, disintegrants, glidants and lubricants, or a mixture of these substances is used as in the external phase. In the process according to the invention, it is also possible to use certain excipients only in the outer phase or only in the inner phase in the granulate.

In the most preferred embodiment of the invention, no binder is used in the preparation of the composition.

In a most preferred embodiment of the invention, 10-50% by weight, preferably 20-40% by weight, most preferably 25-35% by weight of the composition 4-toluenesulfonic acid (1:1) salt of palbociclib having characteristic X-ray powder diffraction peaks the following: Cu Kα (1.1541874 Å) (±0.2° 2θ): 5.18; 10.25; 13.45; 16.08; 21.56, 0.10-1% by weight, preferably 0.20-0.80% by weight, more preferably 0.35-0.80% by weight of letrozole to 50-90% by weight, preferably 55-85% by weight, more preferably 60-80% by weight most preferably 60-70% by weight of microcrystalline cellulose and optionally further excipients, preferably 1-15% by weight, preferably 2-10% by weight, more preferably 2-8% by weight most preferably 5-8% by weight of crospovidone, 0.1-2% by weight %, preferably 0.2-1.5% by weight, 0.5-1.0% by weight of colloid silica and 0.1-3% by weight, preferably 0.5-3.0% by weight, most preferably 1.0-2.5% by weight of magnesium stearate are mixed and the thus obtained mixture homogenized, then the resulting homogenate is granulated by a dry granulation process, preferably by compaction, and optionally further excipients, preferably an additional 0.1-3.0% by weight, preferably 0.5-2.5% by weight, most preferably 1.5-2.5% by weight magnesium stearate and optionally additional 1-15% by weight, preferably 2-10% by weight, most preferably 5-8% by weight of crospovidone is mixed to the obtained granulate and the resulting mixture is filled into a capsule or tableted, and optionally the resulting tablet is coated.

According to a highly preferred embodiment of the invention, the unit doses thus obtained, preferably capsules or tablets, most preferably tablets, are packaged. The packaging material is glass or plastic containers with rubber or plastic lids, or blister packaging, preferably blister packaging. In a particularly preferred embodiment of the invention, the blister comprises not only combination compositions comprising palbocilib tosylate and letrozole, but also a mono composition comprising letrozole. Thus, it is possible to prepare blisters in which the fixed dose combination compositions and letrozole monotherapy formulations are arranged according to the currently used dosing regimen. The 2.5 mg letrozole preparation is a generic product that is available, for example, in tablet form. We can produce a letrozole preparation using the procedures described in patent application CN106580906A or CN106983727A and using the excipients included therein. However, such a product can be prepared, for example, in the form of a tablet by preparing Examples 1 or 2 with omitting palbocilib tosylate from the ingredients.

Pharmaceutical preparations are packaged in according to the present invention are preferably, for example, PVC; PVC/PVdC; duplex Aclar (PVC/ACLAR), triplex Aclar (PVC/PE/ACLAR) blister foil, from OPA/AL/PVC composite film (oriented polyamide/aluminum/polyvinyl chloride film) cold-formed and sealed with an aluminum cover film (so-called cold-blister/CFF, (cold form foil)/), or vapor barrier composite film, for example, the so-called thermoformed from triplex film or PVC/PCTFE film (polyvinyl chloride/polychlorotrifluoroethylene film) and sealed with an aluminum cover film in a blister pack or in a glass with an airtight polyethylene or polypropylene sealing element, in a polyethylene jar or polypropylene jar, preferably PVC; PVC/PVdC; duplex Aclar (PVC/ACLAR), triplex Aclar (PVC/PE/ACLAR) blister foil or OPA/AL/PVC composite film cold-formed and sealed with an aluminum cover foil (so-called cold-blister/CFF/). When blistered, blisters may contain containing only a fixed dose combination of palbociclib tosylate and letrozole but may also contain a composition containing 2.5 mg of letrozole, preferably tablets, suitable for letrozole monotherapy. In the latter case, the fixed combination preparations and the preparations for use in the monotherapy phase containing letrozole are preferably located separately, according to the therapeutic order of administration, in the form described in detail below. But we can also use secondary packaging (e.g. wallet packaging), which includes the blister(s) containing the palbociclib tosylate—letrozole fixed-dose combination preparation and blister(s) containing the letrozole mono-tablet. Such secondary packaging can also be designed in such a way that a so-called the blisters and, where appropriate, information on the use of the product are placed on cardboard.

The process according to the invention can easily be carried out by a person skilled in the art with the equipment and machinery generally known in pharmaceutical technology. Apparatus and procedures, e.g. compaction, granulation, tableting, capsule filling, packaging and related devices are within the general knowledge of the person skilled in the art, but can also be found, for example, in the relevant sections of the Encyclopedia of Pharmaceutical Technology, Third Edition (Informa Healthcare USA, Inc. 270 Madison Avenue New York, N.Y. 10016). Excipients that can be used are commercially available and other useful excipients that do not alter the essence of the invention and their usefulness in preparing the composition of the present invention are well known to those skilled in the art, but these excipients are described in detail in their Handbook of Pharmaceuticals. Excipients, 5th edition (Published by the Pharmaceutical Press Publications division of the Royal Pharmaceutical Society of Great Britain, 1 Lambeth High Street, London SE1 7JN, UK, 100 South Atkinson Road, Suite 206, Grayslake, Ill. 60030-7820, USA and the American Pharmacists Association, 2215 Constitution Avenue, NW, Washington, D.C. 20037-2985, USA). Letrozole is a commercially available pharmaceutical active ingredient. The most preferred palbociclib 4-toluenesulfonic acid of the present invention can be prepared according to the process described in WO17072543 A1, wherein the palbociclib free base is added to an open-chain asymmetric or symmetric ketone, most preferably acetone, most preferably acetone and 4-toluenesulfonic acid monohydrate is added at a temperature between the boiling point of the solvent and preferably at a temperature between room temperature and 80° C., most preferably at 56° C., and the reaction mixture is further stirred, preferably at room temperature for 48 hours. The precipitated crystals were filtered off, washed and dried. The resulting material is stirred in a mixture of a straight chain alcohol type solvent, most preferably ethanol and water, stirred at room temperature for 48 hours, and then the precipitated crystals are filtered off, washed and dried. The preparation is detailed in Reference Example 2.

Another aspect of the invention is a granulate comprising the 4-toluenesulfonic acid salt of brain palbociclib and letrozole. In particular, the granules of the present invention are the 4-toluenesulfonic acid salt of palbociclib and letrozole are not isolated from each other. Preferably, the granulate contains a form of the palbociclib tosylate (1:1) salt, preferably a form of the 4-toluenesulfonic acid (1:1) salt of palbociclib having the following characteristic X-ray powder diffraction positions Cu Kα (1.1541874 Å) (±0.2° 2θ): 5.18; 10.25; 13.45; 16.08; 21.56.

More particularly the granules according to the present invention comprises 10 to 50% by weight, preferably 20 to 40% by weight, most preferably 25 to 35% by weight of palbocyclib tosylate salt, 0.10 to 1% by weight, preferably 0.20 to 0.80% by weight, more preferably contains 0.35-0.80% by weight of letrozole and optionally, in addition to the active ingredients, at least one further excipient, preferably a filler, a binder, a disintegrant and a glidant, or a mixture thereof. As excipients most preferably 50 to 90% by weight, preferably 55 to 85% by weight, more preferably 60 to 80% by weight, most preferably 60 to 70% by weight filler, optionally in an amount of 1 to 10% by weight, preferably 1 to 5% by weight, most preferably 1 to 2% by weight of binder, 1 to 15% by weight, preferably 2 to 12% by weight, most preferably 2 to 8% by weight, more preferably 5-8% by weight of a disintegrant and optionally 0.1-2% by weight, preferably 0.2-1.5% by weight, 0.5-1.0% by weight of glidant and 0.1-3% by weight, preferably 0.5-3.0% by weight, most preferably 1.0-2.5% by weight of lubricant.

The granules according to the invention are preferably dry granules, more preferably compacts, which granules or compacts can be prepared by dry granulation methods or compaction methods known from the prior art. The details of the process and the excipients are described above in the process for preparing the fixed dose combination composition. Some embodiments of the preparation of the compacts of the present invention are described in detail in working Examples 1 and 2 for the preparation of the internal phase. Another aspect of the invention is a blister pack comprising a fixed dose combination composition comprising the 4-toluenesulfonic acid salt of palbociclib and letrozole. More preferably, the blister pack comprises a fixed dose combination composition and an additional pharmaceutical composition comprising one active ingredient, preferably a letrozole.

More preferably, the blister pack contains 28 unit doses or an integer multiple thereof, which unit dose is preferably a tablet or capsule.

A very preferred embodiment of our invention is a blister pack, in which, of the 28 unit doses, 21 are fixed dose combination formulations containing Palbociclib 4-toluenesulfonic acid salt and letrozole and 7 are mono formulations containing letrozole, which formulations are optionally placed in the blister pack to form two separate groups, and, where they contain a multiple of 28 unit doses of the drug, each blister or blister portion containing 28 unit doses of the drug contains 21 fixed-dose combination formulations containing 4-toluenesulphonic acid salt of palbociclib and lethrool and 7 mono formulations containing lethrool, in the same order of distribution.

The blister containing the fixed-dose combination composition comprising the 4-toluenesulfonic acid salt of Palbociclib and letrozole can also be placed in a secondary package, which, in addition to the blister containing the combination preparations, also contains blister/blisters containing a mono preparation, preferably a mono preparation containing letrozole.

Such secondary packaging can be, for example, preferably a box or calendar packaging (wallet package), and in which 21 fixed-dose combination compositions comprising the 4-toluenesulfonic acid salt of Palbociclib and letrozole and 7 compositions comprising letrozole are placed in blisters in such a way that a.) three blisters each contain 7-7 tablets of palbociclib 4-toluenesulfonic acid salt and a fixed-dose combination compositions comprising letrozole, and a fourth blister contains 7 tablets comprising letrozole, or b.) one blister contains 21 fixed-dose combination compositions comprising the 4-toluenesulfonic acid salt of palbociclib and letrozole and another blister contains 7 tablets comprising letrozole, or c.) one blister contains 14 tablets, another contains 7 tablets of palbociclib 4-toluenesulfonic acid salt and a fixed-dose combination compositions comprising letrozole, and a third blister comprises 7 tablets comprising letrozole, or d.) a blister is placed in which, out of the 28 unit doses, 21 are fixed-dose combination compositions comprising Palbociclib 4-toluenesulfonic acid salt and letrozole and 7 are mono compositions comprising letrozole, which are placed in such a way that they form two separate groups in the blister.

The secondary packaging can contain the amount of preparation corresponding to several treatment cycles. In this case, the secondary packaging, which contains integer multiples of the blister arrangements according to points a.)-d.) above. Pharmaceutical compositions are placed in blisters in the form of tablets or capsules. It is also possible to arrange that both the combination and mono preparations are present in the form of tablets or capsules, but it is also possible that one of them is a tablet and the other is a capsule.

Preferably, there is a corresponding marking relating the content of each pharmaceutical composition and/or the time of taking the dose, or the order of taking these compositions on the blisters in the secondary packaging, at the places of every of the individual unit doses on the blister foil or, in the case of wallet packaging, on the blister foil and/or on the packaging (e.g. on the wallboard). The purpose of this is that the patient or whoever is responsible for this can select the next unit dose, clearly follow the dosing cycle and protect against incorrect dosing. At the time of taking the composition, in this notification, we mean the day of the given cycle on which the composition is due to be taken. This marking can be a number, letter, combination of letters or numbers, a graphic sign, preferably an arrow showing a direction, a color, a three-dimensional sign, preferably Braille, but preferably a number, most preferably the number of the day of the cycle from 1 to 28 on which the given composition should be taken.

In another highly preferred embodiment, each row of blister contains 7 unit dose doses, with the first 3 rows containing fixed dose units containing palbociclib 4-tosylate and letrozole and the fourth row containing mono unit doses containing letrozole. If the blister contains a multiple of 28 tablets, preferably the blister also contains the other tablets distributed accordingly in the section consisting of 4 rows containing the next 28 tablets.

According to another highly preferred embodiment, each row of the blister has 7 unit doses, the rows are placed one below the other in such a way that the first 3 rows contain dose units containing palbociclib 4-tosylate and letrozole, and the 4th row contains mono dose units containing letrozole and numbers from 1 to 7 are displayed on the blister foil in place of each unit dose, or whole numbers from 1 to 28 are displayed consecutively on the blister foil in place of each unit dose so that tablets containing palbociclib 4-tosylate and letrozole are given in the row among the serial numbers, numbers 1-21, while mono preparations containing letrozole have serial numbers 22-28. More preferably, the rows containing palbocilib and letrozole dosage units and the row containing letrozole monoproduct are also marked with a different color in addition to the numbering.

According to another very advantageous embodiment of the present invention, blisters are used in which 7 pharmaceutical compositions are located. Such blisters are placed in secondary packaging. Such secondary packaging can be, for example, a box, but it is also advantageous to place the blisters on a cardboard. The secondary packaging preferably contains 3 blisters each containing 7-7 combination compositions containing palbociclib and letrozole and 1 blister containing 7 tablets of letrozole. We can proceed also in such a way that in the secondary package comprises a multiply numbers of combinations compositions blisters having 7-7 compositions comprising palbociclib and letrosol and blisters comprising 7-7 of mono compostions comprising letrozol, e.g. the secondary package comprises 6 blisters of combination compositions and 2 blisters of letrozol.

According to another very advantageous embodiment of our invention, the secondary packaging contains a blister containing 21 compositions comprising palbociclib and letrozole, as well as a blister containing 7 mono compositions of letrozole. Such secondary packaging is preferably a box in which the blisters are placed. Even more preferably, the blisters are attached to a wallboard, so the blisters are so-called they form a wallet package.

If a box is used as secondary packaging, then according to a very advantageous embodiment of our invention, as mentioned above, the dosing sequence is displayed with the markings on the blister(s). When using calendar packaging, the markings can be placed either on the blister or on the cardboard.

In the most preferred embodiment of the present invention, the secondary packaging is a cardboard (e.g. folding carton) consisting of 4 parts, one of which contains the product data, the other a small booklet with patient information, the third a blister containing 21 pieces of the combination product containing palbociclib and letrozole contains, and the 4th contains a blister containing 7 mono compositions containing letrozole and the order of administration is marked on the blister or on the secondary packaging. But we can also proceed in such a way that the cardboard contains 3 blisters that contain 7 combination compositions and 1 blister that contains 7 mono compositions containing letrozole.

The composition of the present invention is an anticancer medicine. It is preferred for the treatment of cancer, especially breast cancer, especially in cases where the cancer is locally advanced (spread nearby) or metastatic (spread to other parts of the body). The composition of the present invention is useful when there are receptors (targets) for certain hormones on the surface of the cancer cells (HR-positive) and they do not produce abnormally high levels of the receptor called HER2 (HER [human epidermal growth factor] negative). In a preferred embodiment of the invention, unit fix dose units comprising of palbociclib 4-tosylate and letrozole are administered for 21 days, then letrozole mono composition is administered from day 22 to day 28 of the therapy, then optionally this 28-day treatment cycle is repeated. In the most preferred embodiment, the treatment is performed with fix dose combination units comprise of palbociclib tosylate based on palbociclib base being preferably 75 mg, 100 mg or 125 mg, the letrozole content of the compositions are 2.5 mg and in mono-unit doses of letrozole comprise 2.5 mg of letrozole.

The advantage of our invention is that we have produced a fixed combination composition comprising palbociclib and letrozole, which makes the combination treatment safe, prevents the person in need of it from taking only one of the two active ingredients, prevents confusion and the administration of a double dose, and also ensures the simultaneous administration, which results in the development of predictable blood level ratios, thus avoiding the possibility of unexpected side effects, which could possibly arise from the administration of the two active substances separated in time.

Further advantage of the combination composition according to the invention is that it can be administered independently of a meal, i.e. both active ingredients have a suitable dissolution profile even in a strongly acidic fasting environment and in a full stomach environment around pH 5.5.

It also allows combination therapy for patients whose stomach has been treated with other medications, e.g. are treated with proton pump inhibitors, so that the low pH characteristic of fasting is never achieved, so that treatment with palbocyclibe, an organic acid and lertrozole would not be possible, since the dissolution of letrozole is inhibited by the e.g. in the presence of succinic acid.

The dissolution results of the active ingredients from the combination composition according to the present invention in pH 4.5 buffer solution are statistically similar those obtained when dissolving the mono formulations from one vessel, which predicts that the fix dose compositions according to the present invention are bioequivalent with the co-administered mono products, thus the parallel administration of mono compositions can be replaced by using the combination composition of the present invention. This requirement cannot be solved with preparations containing dicarboxylic acids that dissolve at pH=4.5 described in the state of the art, because the dissolution of added letrozole is significantly inhibited compared to the dissolution of letrozole administered in a separate composition.

The composition of the present invention can be inexpensive by simple methods. It does not require the use of solvents and thus it has low environmental impact.

The possibility of preparation by simple methods because the active ingredients do not interact surprisingly and thus do not need to be formulated separately in separate phases.

A further great advantage of the present invention is that such blister pack can be prepared using the fixed dose combination compositions of the present invention which comprises a plurality of tablets of different compositions in the order of dosage required for the method of treatment, i.e., 21 units of combination doses of palbocilib and letrozole per blister and 7 formulations of letrozole for monotherapy. By administering them in order, which is preferably provided by the markings on the blister and, if appropriate, the accompanying description, the risk of incorrect dosing can be minimized. This is particularly useful and cannot be accomplished using compositions known in the art.

Figure 1:
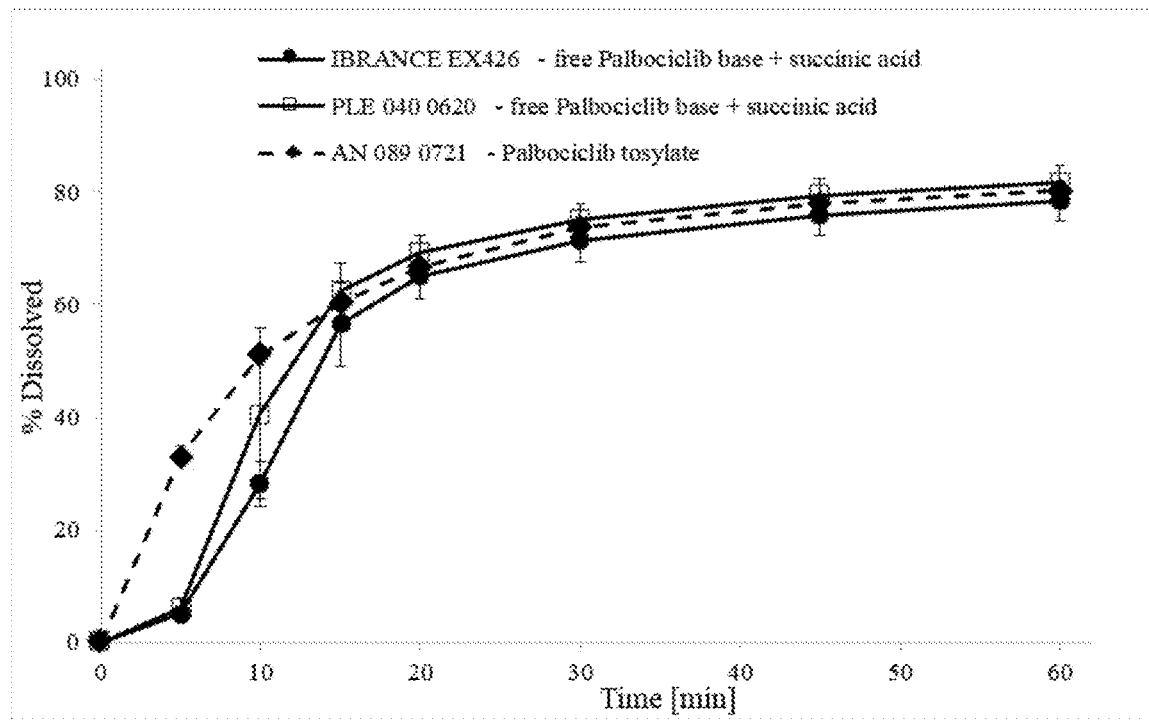
FIG. 1: Palbociclib dissolution curves in pH 4.5 buffer: PLE0400621 (Example R-2), AN0890721 (WE-1/C) and IBRANCE tablets

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding Hungarian application No. P2200147, filed May 10, 2022, are incorporated by reference herein.

The invention is illustrated in detail by the following examples, without limiting the scope of the invention to the following examples:

Active pharmaceutical ingredient:

REFERENCE EXAMPLES

Example R-1: Preparation of Palbociclib 4-toluenesulfonate salt (1:1)

Palbocycl base (1.0 g, 2.23 mmol), acetone (20 mL) and water (4 mL) were added to an vessel having intensive stirrer, and 4-toluenesulfonic acid monohydrate (424.2 mg, 2.23 mmol) was added at reflux temperature. The solution was cooled to room temperature, stirred for 48 hours, then the crystalline product was filtered, washed with a little cold acetone-water and air dried.

The resulting mixture was stirred in a mixture of ethanol (20 ml) and water (0.2 ml) at room temperature for 48 hours, then the crystalline product was filtered off, washed with a little cold acetone and air-dried.

Yield: 0.85 g (62.9%)

Mp.: no characteristic value, thermal decomposition occurs above 250° C.

Analysis calculated for C31H39N7O5S (621.76):
Calculated C: 59.89% H: 6.32% N: 15.77% S: 5.16%
Measured C: 59.69% H: 6.08% N: 15.46% S: 5.69%

$^1$H-NMR (DMSO-$d_6$, 400 MHz): 10.26 (bs, 1H), 8.97 (s, 1H), 8.71 (b, 2H), 8.12 (d, J=2.8 Hz, 1H), 7.91 (d, J=9.1 Hz, 1H), 7.57 (dd, J1=2.9 Hz, J2=9.1 Hz, 1H), 7.48 (~d, J=8.0 Hz, 2H), 7.12 (~d, J=8.4 Hz, 2H), 5.83 (m, 1H), 3.37 (m, 4H), 3.29 (m, 4H), 2.43 (s, 3H), 2.32 (s, 3H), 2.29 (s, 3H), 2.25 (m, 2H), 1.89 (m, 2H), 1.78 (m, 2H), 1.59 (m, 2H).

$^{13}$C-NMR (DMSO-$d_6$, 125 MHz): 202.62, 160.390, 158.62, 158.40, 154.94, 145.86, 145.45, 142.47, 142.21, 137.82, 135.98, 129.64, 128.25, 126.06, 125.67, 115.26, 106.98, 53.11, 45.87, 42.87, 31.49, 27.75, 25.32, 20.96, 13.84.

Figure 3:
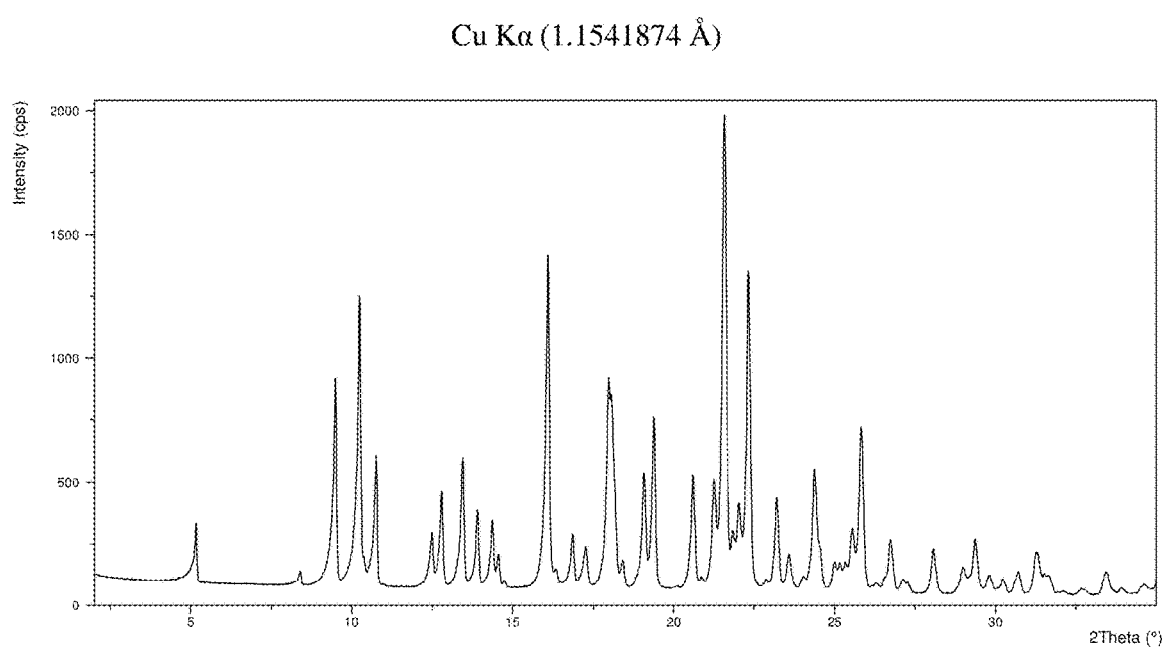
FIG. 3: XRD pattern of the 4-toluenesulfonic acid (1:1) salt of Palbociclib.
Figure 4:
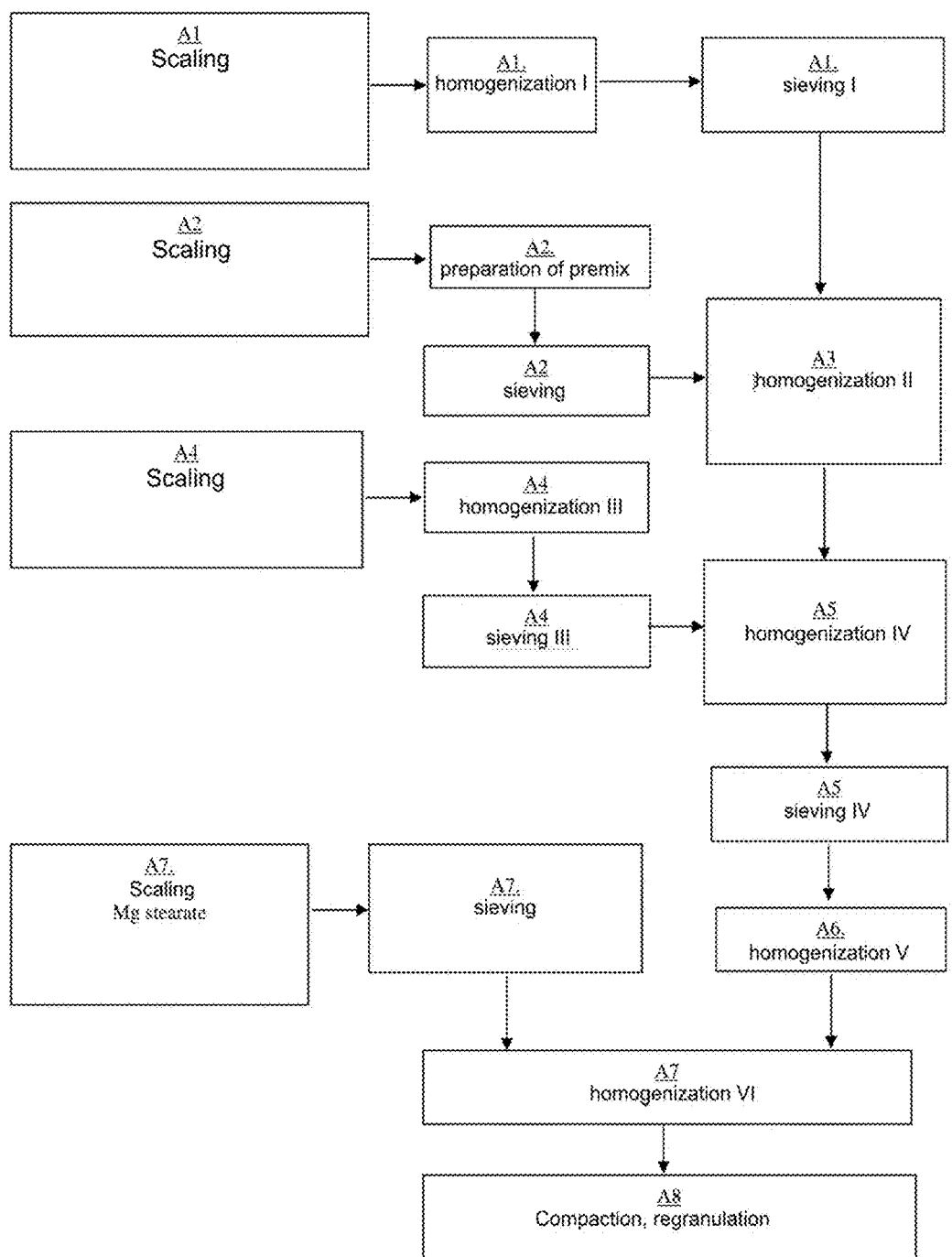
FIG. 4: Flow chart for preparing the granules described in the examples.
Figure 5:
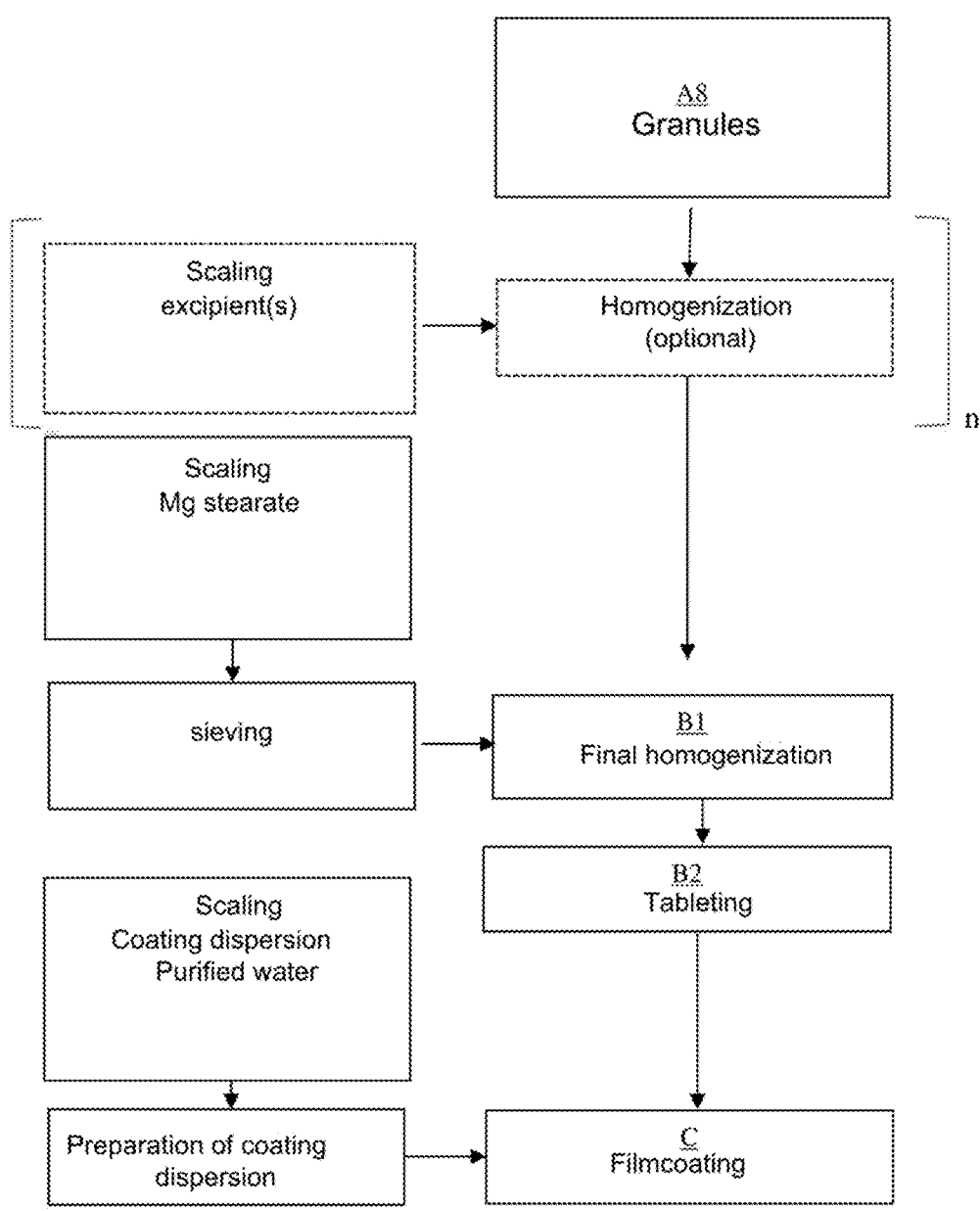
FIG. 5: Flow chart of tablet preparation described in the examples.
Figure 6A:
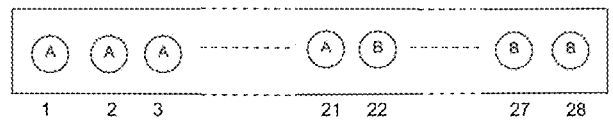
FIG. 6A: Blister pack form in which A is the location of the fixed dose combination formulation containing palbociclib tosylate and letrozole and B is the location of the letrozole mono formulation.
Figure 6B:
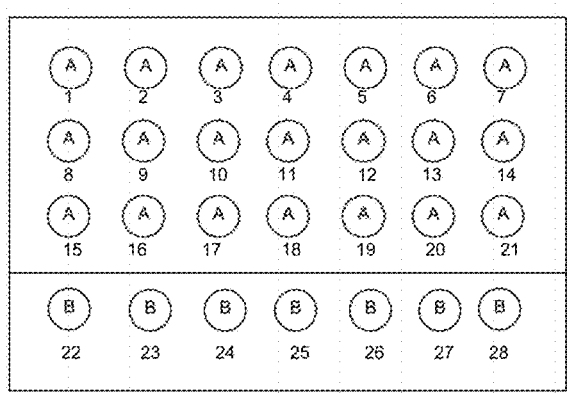
FIG. 6B: Blister pack form in which A is the location of the fixed dose combination formulation containing palbociclib tosylate and letrozole and B is the location of the letrozole mono formulation and the serial number below the tablets is the day of the cycle.
Figure 6C:
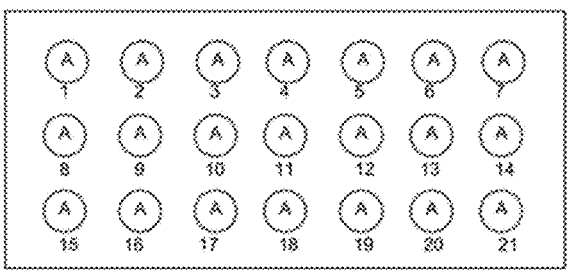
FIG. 6C: A blister combination consisting of a blister containing 21 combination preparations and a blister containing 7 letrozole monopreparations.
Figure 6C:
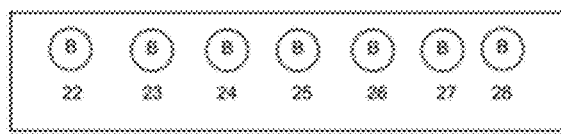
Figure 7:
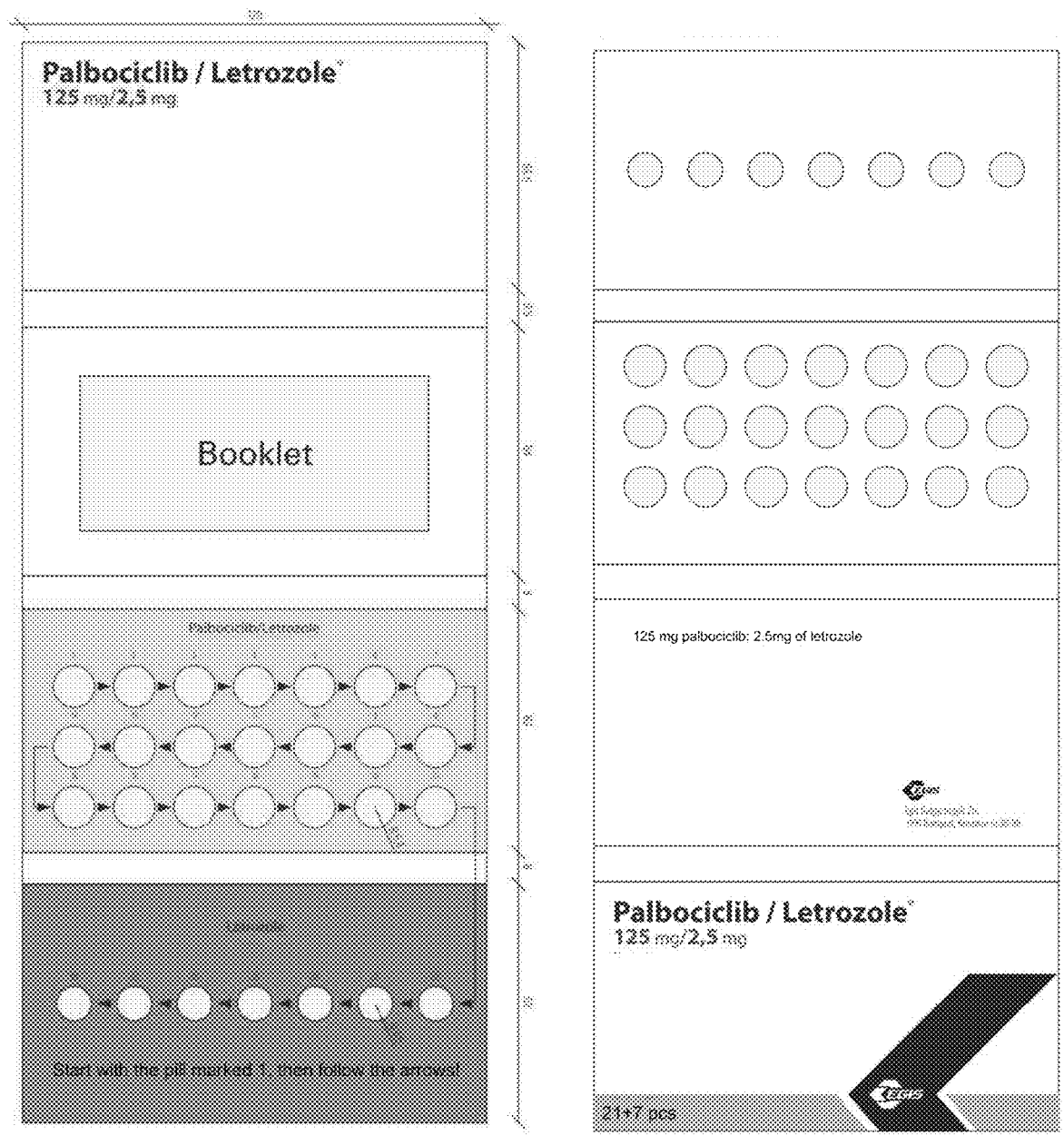
FIG. 7: Wallet (calendar) packaging plan

X-ray powder diffraction peaks are as follows: Cu Kα (1.1541874 Å) (±0.2° 2θ): 5.18; 10.25; 13.45; 16.08; 21.56. In particular, it can be characterized by the following X-ray powder diffraction peaks: 2θ (±0.2° 2θ): 5.18; 9.49; 10.25; 10.76; 13.45; 16.08; 17.97; 19.39; 21.56; 22.33. More specifically, it can be characterized by the following X-ray powder diffraction peaks: 2θ (±0.2° 2θ): 5.18; 8.40; 9.49; 10.25; 10.76; 12.48; 12.80; 13.45; 13.92; 14.37; 14.56; 16.08; 16.86; 17.27; 17.97; 18.39; 19.07; 19.39; 20.59; 21.25; 21.56; 22.03; 22.33; 23.21; 23.57; 24.37; 24.99; 25.55; 25.82; 26.72; 27.10; 28.05; 28.99; 29.35; 29.78; 30.21; 30.71; 31.26; 33.43. Its typical X-ray powder diffractogram is shown in FIG. 3, and signals with an intensity greater than 1% are summarized in the table below:

X-ray powder diffraction data of palbociclib
4-toluenesulfonic acid (1:1) salt modification
(relative intensities >1%)

| Peak | 2θ (°) | d (Å) | (relative intensities >1%) (%) |
|---|---|---|---|
| 1 | 5.18 | 17.06 | 10 |
| 2 | 8.40 | 10.52 | 2 |
| 3 | 9.49 | 9.31 | 36 |
| 4 | 10.25 | 8.62 | 55 |
| 5 | 10.76 | 8.22 | 25 |
| 6 | 12.48 | 7.09 | 9 |
| 7 | 12.80 | 6.91 | 17 |
| 8 | 13.45 | 6.58 | 23 |
| 9 | 13.92 | 6.36 | 14 |
| 10 | 14.37 | 6.16 | 14 |
| 11 | 14.56 | 6.08 | 4 |
| 12 | 16.08 | 5.51 | 65 |
| 13 | 16.86 | 5.25 | 10 |
| 14 | 17.27 | 5.13 | 11 |
| 15 | 17.97 | 4.93 | 42 |
| 16 | 18.39 | 4.82 | 4 |
| 17 | 19.07 | 4.65 | 25 |
| 18 | 19.39 | 4.57 | 30 |
| 19 | 20.59 | 4.31 | 22 |
| 20 | 21.25 | 4.18 | 18 |
| 21 | 21.56 | 4.12 | 100 |
| 22 | 22.03 | 4.03 | 29 |
| 23 | 22.33 | 3.98 | 57 |
| 24 | 23.21 | 3.83 | 19 |
| 25 | 23.57 | 3.77 | 9 |
| 26 | 24.37 | 3.65 | 31 |
| 27 | 24.99 | 3.56 | 6 |
| 28 | 25.55 | 3.48 | 16 |
| 29 | 25.82 | 3.45 | 31 |
| 30 | 26.72 | 3.33 | 11 |
| 31 | 27.10 | 3.29 | 3 |
| 32 | 28.05 | 3.18 | 9 |
| 33 | 28.99 | 3.08 | 7 |
| 34 | 29.35 | 3.04 | 13 |
| 35 | 29.78 | 3.00 | 5 |
| 36 | 30.21 | 2.96 | 3 |
| 37 | 30.71 | 2.91 | 3 |
| 38 | 31.26 | 2.86 | 11 |
| 39 | 31.53 | 2.84 | 5 |
| 40 | 33.43 | 2.68 | 6 |

General Procedure for the Preparation of Tablets According to R-2, Working Example 1 and Working Example 2:

Briefly, the inner phase is prepared and granulated, the resulting granulate is mixed with the materials of the outer phase and tableted.

In detail:

A) Production of inner phase:

A1. Preparation of homogenate I:

Poliplasdone XL-10 GAF, Aerosil 200, and one-third of the amount of microcrystalline cellulose (PH 101 FMC) used in the formulation were weighed into a homogenizer and homogenized.

The resulting homogenate is sieved through an oscillating regranulation with a 0.8 mm screen.

A2. Preparation of a premix containing letrozole:

Letrozole sand the second third of the microcrystalline cellulose (PH 101 FMC) used in the formulation was homogenized in a polyethylene bag. The premix thus obtained is sieved through an acid-proof hand sieve with a sieve spacing of 0.5 mm.

A3. Preparation of homogenate II:

The homogenate I prepared in step A1 and the letrozole-containing premix prepared in the second step are weighed into a barrel homogenizer, and the resulting mixture is homogenized.

A4. Preparation of Homogenate III: The active ingredient palbociclib * and one third of the amount of microcrystalline cellulose (PH 101 FMC) used in the formulation are homogenized in a homogenizer. The homogenate thus obtained is sieved on an oscillating regranulator using a sieve spacing of 0.8 mm.

(* For R-2, Balbociclib base is used, for Working examples 1 and 2, palbociclib tosylate is used)

A5. Preparation of homogenate IV:

The A3. Homogenate II prepared in accordance with point A4, and the homogenate III was charged to a barrel homogenizer and the resulting mixture was homogenized. The resulting homogenate was sieved on an oscillating regranulator using a sieve spacing of 0.8 mm.

A6. Preparation of homogenate V:

The A5. The homogenate of point IV is rehomogenized in a barrel homogenizer

A7. Preparation of homogenate VI:

The A6. The homogenate V and the homogenate V, previously sieved through an acid-resistant hand sieve with a yarn spacing of 0.5 mm, are charged to a homogenizer carrying half the amount of magnesium stearate used in the composition, and the resulting mixture is homogenized.

A8. Granulation:

The A7. The homogenate VI is filled into the feed hopper of the compactor and compacted.

B) Tablet production:

B1. Preparation of final homogenate:

The excipients used in the composition are added to the granules prepared in A8. step in accordance with the table below in a barrel homogenizer and the thus given mixture is homogenized before adding the next excipient.

B2. Tableting:

A B1. The final homogenate prepared according to the above is added to the funnel of a tableting machine and tableted.

C. Coating:

The tablets of B2, are poured into the coating pan and the temperature of the outlet air is heated to 39-45° C. while the vessel is rotated intermittently, and the coating suspension is sprayed onto the tablets.

Preparation of Coating Suspension:

Purified water is measured in a beaker and stirred at such a rate that a liquid funnel is formed without air bubbles. The coating material (Vivacoat PA-3P-468) should be sprayed into the liquid funnel. After adding the entire amount of material, the stirring speed should be reduced until the liquid funnel disappears. The resulting dispersion is filtered through a 0.4 mm acid-proof sieve. The thus obtained coating suspension is stirred until and during the use.

The following experiments were performed with using Vivacoat PA-3P-468, a commercially available coating material having the following composition:

| | quality | composition |
|---|---|---|
| Hypromellose (HPMC) 6 | Ph.Eur./USP/E464 | 39.00% |
| Titanium dioxide | Ph.Eur./USP/E171 | 23.00% |
| Talc | Ph.Eur./NF/E553b | 16.36% |
| Polydextrose | E1200 | 15.00% |
| Polyethylene glycol (PEG) 3350 | Ph.Eur./USP | 6.00% |
| Ferrosoferric oxide black | NF/E172 | 0.22% |
| Indigotine LK | E132 | 0.18% |
| Carmine DYE | E120 | 0.14% |
| Ferric oxide red | NF/E172 | 0.10% |

The tools used in the examples are:

Homogenization: barrel homogenizer, QUICKBIN 22 homogenizer, using 5 or 10 l barrels at 17 rpm for 3-5 minutes.

Sieving: If a non-acid-resistant hand sieve is used, a Frewitt MF LAB oscillating regranulator with a 0.8 mm sieve insert at 110-140 rpm was used.

Granulation: Fitzpatrik CCS-220 dry granulator isolator is used to control the particle size with the following settings:

Regranulation sieve (perforated plate) 1.0 mm preforation

| Dry granulator data | |
|---|---|
| Roller set | knurled |
| Regranulation unit | cutler |

| Operational parameters | |
|---|---|
| Operation | Prescribed parameter to set |
| Horizontal feed screw speed (HFS) | 12-16 rpm (recommended: 14 rpm) |
| Vertical feed screw speed (VFS) | 90-110 rpm (recommended: 100 rpm) |
| Distance of rollers | 1.00-1.50 mm (recommended: 1.25 mm) |
| Roller force | 9.5-10.5 kN/cm (recommended: 10 kN/cm) |
| Roller speed | 2.5-3.5 rpm (recommended: 3 rpm) |
| Regranulator speed | 1000-1200 rpm (recommended: 1100 rpm) |
| Duration of the operation | approx. 30 minutes |

Tableting:

| Device type: | Dott Bonapace tableting isolator |
|---|---|
| Press tool data: | |
| Mold shape: | oblong, concave |
| Length: | ~16.0 mm |
| Width: | ~8.5 mm |
| Number of press tools: | 8 |
| Table speed: | |
| Maximum allowed: | 12/minutes |
| Recommended: | 10/minutes |
| Forced feed speed: | |
| Recommended: | 8/minutes |

Example R-2

Comparative Formulation Containing 125 mg of Palbociclib Base, 2.5 mg of Letrozole and Succinic Acid

| Batch No.: PLE 040 0620 Palbociclib/Letrozol filmtablet 125/2.5 mg | |
|---|---|
| | 125/2.5 mg mg/ftbl |
| Inner phase (kompaktum) | |
| Palbociclib base | 125.00 |
| Letrozole | 2.50 |
| Cellulose, Microcrystalline | 364.50 |
| Crospovidone | 18.00 |
| Silica, Colloidal Anhydrous | 3.00 |
| Magnesium Stearate | 3.00 |
| Outer phase | |
| Succinic acid | 60.00 |
| Crospovidone | 18.00 |
| Magnesium Stearate | 6.00 |
| Tablet core | 600.00 |
| Film coating | 18.00 |
| Filmtablet | 618.00 |

Brief Process for Preparation of Tablets:

Tablets were prepared according to the general procedure above, except that the final homogenate was prepared as follows:

The granules and the succinic acid used in the external phase are weighed and homogenized in a barrel homogenizer. To the homogenate thus obtained was added the Poliplasdone XL-10 GAF used in the outer phase and the resulting mixture was homogenized, and then charged to a homogenizer carrying half the amount of magnesium stearate used in the composition, previously sieved through an acid-resistant hand sieve with a span of 0.5 mm. The resulting mixture is homogenized.

Working Examples According to the Invention:

Working Example 1: Preparation of Film-Coated Tablets Containing Palbociclib Tosylate and Letrozole with Different Drug Ratios

| Palbociclib/Letrozol filmtablet | | | |
|---|---|---|---|
| | WE-1/A 75/2.5 mg | WE-1/B 100/2.5 mg mg/ftbl | WE-1/C AN0890721 125/2.5 mg |
| Inner phase (kompaktum) | | | |
| Palbociclib tozilát | 103.875 | 138.50 | 173.125 |
| Letrozole | 2.50 | 2.50 | 2.50 |
| Cellulose. Microcrystalline | 219.425 | 293.40 | 367.375 |
| Crospovidone | 18.00 | 24.00 | 30.00 |
| Silica. Colloidal Anhydrous | 1.80 | 2.40 | 3.00 |
| Magnesium Stearate | 3.60 | 4.80 | 6.00 |
| Outer phase | | | |
| Crospovidone | 7.20 | 9.60 | 12.00 |
| Magnesium Stearate | 3.60 | 4.80 | 6.00 |
| Tablet core | 360.00 | 480.00 | 600.00 |
| Filmcoating | 14.40 | 19.20 | 24.00 |
| Filmtablet | 374.40 | 499.20 | 624.00 |

Brief Process for Preparation of Tablets:

Tablets were prepared according to the general procedure above, except that the final homogenate was prepared as follows:

The granules and the Poliplasdone XL-10 GAF used in the external phase are weighed and the resulting mixture is homogenized in a barrel homogenizer, then the resulting mixture is charged to a homogenizer carrying half the amount of magnesium stearate used in the composition, which was previously sieved through an acid-resistant hand sieve with a sieve spacing of 0.5 mm, and the resulting mixture is homogenized.

Working Example 2: Preparation of Film-Coated Tablets Containing Palbociclib Tosylate and Letrozole with Different Drug Ratios

| Palbociclib/Letrozol filmtablet | | | |
|---|---|---|---|
| | WE-2/A 75/2.5 mg | WE-2/B 100/2.5 mg mg/ftbl | WE-2/C 125/2.5 mg |
| Inner phase (kompaktum) | | | |
| Palbociclib tozilát | 103.875 | 138.50 | 173.125 |
| Letrozole | 2.50 | 2.50 | 2.50 |
| Cellulose. Microcrystalline | 237.425 | 317.40 | 397.375 |
| Crospovidone | 7.20 | 9.60 | 12.00 |
| Silica. Colloidal Anhydrous | 1.80 | 2.40 | 3.00 |
| Magnesium Stearate | 3.60 | 4.80 | 6.00 |
| Outer phase fázis | | | |
| Magnesium Stearate | 3.60 | 4.80 | 6.00 |
| Tablet core | 360.00 | 480.00 | 600.00 |
| Film coating | 14.40 | 19.20 | 24.00 |
| Filmtablet | 374.40 | 499.20 | 624.00 |

Brief Process for Preparation of Tablets:

Tablets were prepared according to the general procedure above, except that the final homogenate was prepared by loading the granulate and a homogenizer carrying half the amount of magnesium stearate used in the composition, previously sieved through an acid-resistant hand sieve with a sieve spacing of 0.5 mm, and the resulting mixture is homogenized.

Example 3 Dissolution Tests

The studies were conducted by the Guidance for Industry; 10740430 FNL08/09/2018 Dissolution testing and acceptance criteria for high solubility pharmaceutical preparations in immediate release solid oral dosage form; DHHS, FDA, CDER; 2018. The dissolution test was performed on a USP 2 device, and the concentration of the dissolved drug was measured by UHPLC on the following equipment:

Equipment: Waters H-Class UPLC:
Column: Waters Acquity BEH C18, 2.1×50 mm, 1.7 μm
Solvent (Diluent): 0.2% perchloric acid solution/Acetonitrile=50/50 (V/V %)
Eluent: A: 0.1% perchloric acid solution
B: Acetonitrile
Gradient profile:

| Time [min] | Eluent A [%] | Eluent B [%] |
|---|---|---|
| kezdeti | 80 | 20 |
| 1.7 | 65 | 35 |
| 2.0 | 10 | 90 |
| 3.1 | 10 | 90 |
| 3.2 | 80 | 20 |
| 4.5 | 80 | 20 |

Flow rate: 0.6 mL/min
Column temperature: 38° C.
Column pressure: ~620 bar
Sample temperature: 20° C.
Injected sample: 3.0 μL
Detection: UV, 300 nm Palbociclib; 240 nm Letrozole
Evaluation: External standard calibration method based on peak areas K-1: Investigation of Palbociclib Dissolution The reference formulation of Example R-2, a formulation containing palbociclib tosylate and letrozole prepared by the E-1/C method, and an IIBRANCE tablet containing palbociclib base and succinic acid were compared.

The results are shown in FIG. 1.

The measurement method: The dissolution rate was determined in each case in 500 ml of 10 mM sodium acetate buffer at pH 5.5 in a USP 2 with a rotating paddle at 50 rpm.

The reference product is Ibrance 125 mg film-coated tablets containing Palbociclib base and succinic acid; serial number: EX 4261. The test products are Palbociclib-Letrozole 125 mg/2.5 mg film-coated tablets containing Palbociclib base and succinic acid; Serial No. PLE0400620 and Palbociclib-Letrozole 125 mg/2.5 mg film-coated tablets containing Palbociclib tosylate; batch number: AN0890721

The results are summarized in the table below:

TABLE 1

| Dissolution data of Palbociclib - Ibrance EX4261 | | | | | | | |
|---|---|---|---|---|---|---|---|
| Batch No: EX4261 | Dissolved [%] - Palbociclib Time (min) | | | | | | |
| Units (n) | 5 | 10 | 15 | 20 | 30 | 45 | 60 |
| 1 | 6.04 | 22.66 | 47.67 | 63.98 | 71.74 | 76.91 | 79.84 |
| 2 | 6.09 | 32.15 | 62.41 | 68.47 | 73.75 | 78.04 | 80.34 |
| 3 | 5.51 | 33.47 | 60.46 | 67.56 | 72.86 | 77.03 | 79.88 |
| 4 | 4.59 | 26.00 | 59.09 | 64.01 | 70.96 | 75.79 | 78.45 |
| 5 | 5.29 | 26.99 | 46.65 | 57.80 | 64.07 | 68.67 | 71.39 |
| 6 | 3.16 | 28.19 | 62.80 | 68.94 | 74.34 | 77.86 | 80.58 |
| Mean [%] | 5.1 | 28.2 | 56.5 | 65.1 | 71.3 | 75.7 | 78.4 |
| SD | 1.10 | 4.01 | 7.38 | 4.19 | 3.75 | 3.54 | 3.52 |
| RSD [%] | 21.6 | 14.2 | 13.1 | 6.4 | 5.3 | 4.7 | 4.5 |
| Min. [%] | 3.2 | 22.7 | 46.7 | 57.8 | 64.1 | 68.7 | 71.4 |
| Max. [%] | 6.1 | 33.5 | 62.8 | 68.9 | 74.3 | 78.0 | 80.6 |
| Conf. Lim (p = 0.95) | 1.2 | 4.2 | 7.7 | 4.4 | 3.9 | 3.7 | 3.7 |

TABLE 2

Dissolution data of Palbociclib - PLE 040 0620

| Batch No:<br>PLE 040 0620 | Dissolved [%] - Palbociclib<br>Time (min) | | | | | | |
|---|---|---|---|---|---|---|---|
| Units (n) | 5 | 10 | 15 | 20 | 30 | 45 | 60 |
| 1 | 8.05 | 49.34 | 65.15 | 69.95 | 74.68 | 78.16 | 80.18 |
| 2 | 7.78 | 31.81 | 56.88 | 64.12 | 70.58 | 74.96 | 77.66 |
| 3 | 5.74 | 34.10 | 61.50 | 68.77 | 74.92 | 79.35 | 82.18 |
| 4 | 6.06 | 53.05 | 67.81 | 73.13 | 78.48 | 82.11 | 84.17 |
| 5 | 5.57 | 57.60 | 66.54 | 70.73 | 74.73 | 77.96 | 79.94 |
| 6 | 2.92 | 18.42 | 56.66 | 68.74 | 77.81 | 83.37 | 86.04 |
| Mean [%] | 6.0 | 40.7 | 62.4 | 69.2 | 75.2 | 79.3 | 81.7 |
| SD | 1.85 | 15.05 | 4.86 | 2.98 | 2.81 | 3.05 | 3.06 |
| RSD [%] | 30.8 | 37.0 | 7.8 | 4.3 | 3.7 | 3.8 | 3.7 |
| Min. [%] | 2.9 | 18.4 | 56.7 | 64.1 | 70.6 | 75.0 | 77.7 |
| Max. [%] | 8.1 | 57.6 | 67.8 | 73.1 | 78.5 | 83.4 | 86.0 |
| Conf. Lim (p = 0.95) | 1.9 | 15.8 | 5.1 | 3.1 | 2.9 | 3.2 | 3.2 |

TABLE 3

Dissolution data of Palbociclib - AN 089 0721

| Batch No:<br>AN 089 0721 | Dissolved [%] - Palbociclib<br>Time (min) | | | | | | |
|---|---|---|---|---|---|---|---|
| Units (n) | 5 | 10 | 15 | 20 | 30 | 45 | 60 |
| 1 | 34.17 | 50.95 | 59.71 | 65.61 | 71.77 | 76.56 | 78.96 |
| 2 | 33.00 | 49.13 | 60.01 | 66.44 | 73.21 | 78.36 | 80.37 |
| 3 | 34.36 | 51.90 | 61.26 | 66.70 | 72.68 | 76.76 | 79.54 |
| 4 | 33.59 | 51.99 | 61.98 | 68.24 | 75.19 | 79.13 | 81.77 |
| 5 | 33.63 | 52.78 | 61.36 | 67.21 | 74.95 | 78.82 | 81.29 |
| 6 | 29.65 | 48.75 | 58.02 | 65.82 | 73.67 | 78.05 | 80.14 |
| Mean [%] | 33.1 | 50.9 | 60.4 | 66.7 | 73.6 | 77.9 | 80.3 |
| SD | 1.74 | 1.64 | 1.45 | 0.97 | 1.32 | 1.07 | 1.05 |
| RSD [%] | 5.3 | 3.2 | 2.4 | 1.5 | 1.8 | 1.4 | 1.3 |
| Min. [%] | 29.7 | 48.8 | 58.0 | 65.6 | 71.8 | 76.6 | 79.0 |
| Max. [%] | 34.4 | 52.8 | 62.0 | 68.2 | 75.2 | 79.1 | 81.8 |
| Conf. Lim (p = 0.95) | 1.8 | 1.7 | 1.5 | 1.0 | 1.4 | 1.1 | 1.1 |

It is clear from the results that palbociclib is similarly dissolved from all three formulations.

K-2 Letrozole Dissolution Test:

The reference products are Ibrance 125 mg film-coated tablets containing Palbociclib base and succinic acid; Serial No. EX 4261 and Femara 2.5 mg film-coated tablets containing letrozole; dissolution of SNT20 was performed together in the same vessel. The test product was Palbociclib-Letrozole 125 mg/2.5 mg film-coated tablets containing Palbociclib base and succinic acid (PLE0400620) and Palbociclib-Letrozole 125 mg/2.5 mg film-coated tablets containing Palbociclib-tosylate and letrozole (AN0890721).

Figure 2:
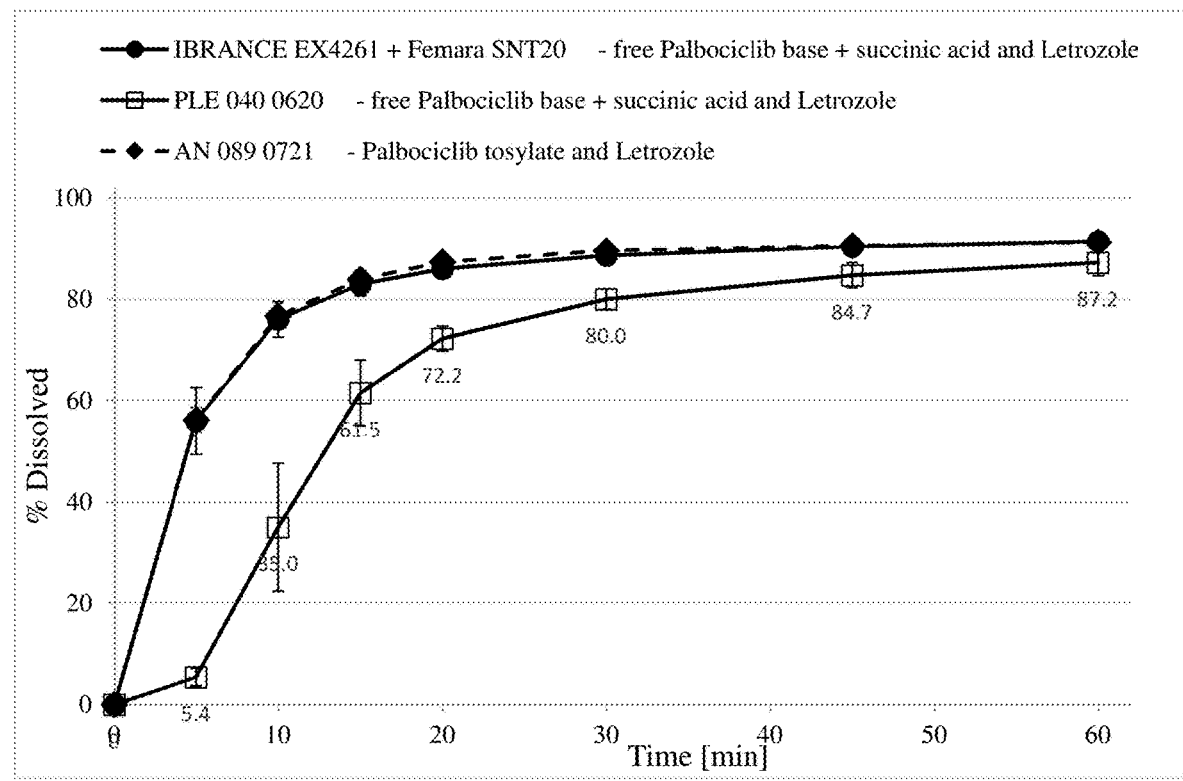
FIG. 2: Dissolution curves of letrozole in pH 4.5 buffer: Dissolution of PLE0400621 (Example R-2) and AN0890721 (Example WE-1/C) and IBRANCE tablets and Femara tablets in a container.

Dissolution results are shown in FIG. 2 and the data in the tables below

TABLE 4

Dissolution data of Letrozole - Femara SNT20

| Batch No: SNT20 | Dissolved [%] - Letrozole<br>Time (min) | | | | | | |
|---|---|---|---|---|---|---|---|
| Units (n) | 5 | 10 | 15 | 20 | 30 | 45 | 60 |
| 1 | 52.97 | 75.45 | 83.39 | 86.03 | 88.19 | 90.12 | 90.57 |
| 2 | 48.43 | 70.62 | 79.23 | 83.66 | 86.79 | 88.59 | 89.35 |
| 3 | 60.41 | 78.35 | 84.06 | 86.90 | 89.19 | 91.10 | 92.27 |
| 4 | 49.53 | 73.43 | 81.66 | 85.10 | 88.10 | 90.16 | 91.26 |
| 5 | 60.33 | 78.05 | 83.33 | 85.80 | 88.36 | 89.51 | 90.98 |
| 6 | 64.31 | 80.02 | 85.92 | 88.43 | 91.24 | 93.16 | 94.33 |
| Mean [%] | 56.0 | 76.0 | 82.9 | 86.0 | 88.6 | 90.4 | 91.5 |
| SD | 6.57 | 3.51 | 2.28 | 1.61 | 1.49 | 1.57 | 1.70 |
| RSD [%] | 11.7 | 4.6 | 2.8 | 1.9 | 1.7 | 1.7 | 1.9 |
| Min. [%] | 48.4 | 70.6 | 79.2 | 83.7 | 86.8 | 88.6 | 89.4 |
| Max. [%] | 64.3 | 80.0 | 85.9 | 88.4 | 91.2 | 93.2 | 94.3 |
| Conf. Lim (p = 0.95) | 6.9 | 3.7 | 2.4 | 1.7 | 1.6 | 1.6 | 1.8 |

TABLE 5

Dissolution data of Letrozole - PLE 040 0620

| Batch No: PLE 040 0620 | Dissolved [%] - Letrozole Time (min) | | | | | | |
|---|---|---|---|---|---|---|---|
| Units (n) | 5 | 10 | 15 | 20 | 30 | 45 | 60 |
| 1 | 7.18 | 41.48 | 64.83 | 72.46 | 79.06 | 82.93 | 84.87 |
| 2 | 7.14 | 29.20 | 57.86 | 69.29 | 77.57 | 83.27 | 87.02 |
| 3 | 5.48 | 30.43 | 60.79 | 72.58 | 80.99 | 86.40 | 89.34 |
| 4 | 5.36 | 43.61 | 67.60 | 75.92 | 82.76 | 86.84 | 88.55 |
| 5 | 4.48 | 50.26 | 67.00 | 73.24 | 78.18 | 81.46 | 83.46 |
| 6 | 2.61 | 15.03 | 50.70 | 69.64 | 81.21 | 87.50 | 90.07 |
| Mean [%] | 5.4 | 35.0 | 61.5 | 72.2 | 80.0 | 84.7 | 87.2 |
| SD | 1.72 | 12.67 | 6.46 | 2.46 | 2.01 | 2.49 | 2.61 |
| RSD [%] | 31.9 | 36.2 | 10.5 | 3.4 | 2.5 | 2.9 | 3.0 |
| Min. [%] | 2.6 | 15.0 | 50.7 | 69.3 | 77.6 | 81.5 | 83.5 |
| Max. [%] | 7.2 | 50.3 | 67.6 | 75.9 | 82.8 | 87.5 | 90.1 |
| Conf. Lim (p = 0.95) | 1.8 | 13.3 | 6.8 | 2.6 | 2.1 | 2.6 | 2.7 |

TABLE 6

Dissolution data of Letrozole - AN 089 0721

| Batch No: AN 089 0721 | Dissolved [%] - Letrozole Time (min) | | | | | | |
|---|---|---|---|---|---|---|---|
| Units (n) | 5 | 10 | 15 | 20 | 30 | 45 | 60 |
| 1 | 57.88 | 77.24 | 83.72 | 86.64 | 88.69 | 89.71 | 90.58 |
| 2 | 56.13 | 73.09 | 83.45 | 86.95 | 89.16 | 90.21 | 90.44 |
| 3 | 57.52 | 77.43 | 83.88 | 86.31 | 87.96 | 89.09 | 90.00 |
| 4 | 57.41 | 79.30 | 86.11 | 88.82 | 91.12 | 92.04 | 93.20 |
| 5 | 56.78 | 78.78 | 85.01 | 87.38 | 89.56 | 90.27 | 90.83 |
| 6 | 51.33 | 74.07 | 81.19 | 87.57 | 91.10 | 92.13 | 92.77 |
| Mean [%] | 56.2 | 76.7 | 83.9 | 87.3 | 89.6 | 90.6 | 91.3 |
| SD | 2.45 | 2.52 | 1.66 | 0.89 | 1.29 | 1.24 | 1.34 |
| RSD [%] | 4.4 | 3.3 | 2.0 | 1.0 | 1.4 | 1.4 | 1.5 |
| Min. [%] | 51.3 | 73.1 | 81.2 | 86.3 | 88.0 | 89.1 | 90.0 |
| Max. [%] | 57.9 | 79.3 | 86.1 | 88.8 | 91.1 | 92.1 | 93.2 |
| Conf. Lim (p = 0.95) | 2.6 | 2.6 | 1.7 | 0.9 | 1.4 | 1.3 | 1.4 |

Evaluation of K-1 and K-2 dissolution experiments:

For immediate-release solid oral formulations containing a high solubility drug, the dissolution criterion is Q=80% over 30 minutes according to the above-mentioned Guideline, where Q is the amount of drug dissolved as a percentage of the indicated content per dosage unit. The requirement of section 1 (n=6) is met if each unit is not less than Q+5% of the dissolution test.

Based on this, it can be concluded that the dissolution of palbociclib (K-1 experiment) is achieved for both combination products and IBRANCE using pH 5.5 buffer under standard conditions.

However, we have shown that with the recommended standard dissolution test conditions to increase gastric pH (500 ml of 10 mM sodium acetate buffer at pH 5.5 in a USP 2, 50 rpm paddle), the dissolution requirement for letrozole is limited to Palbociclib tosylate in fixed-dose formulation with letrozole and the co-administered mono Palbociclib and mono Letrozole tablets. However, the dissolution criterion is not met for a fixed-dose combination of Letrozole and Palbociclib base if the formulation contains succinic acid which is used for improve the dissolution of palbociclib base.

Example 4: Testing the Moisture Content of a Preparation

The water content of the formulations was determined by a Karl-Fisher titration coulometric method connected to an oven. In the initial state, a water content of 3.0-3.5% was measured at room temperature. Stored in an HDPE container with silica gel.

Example 5: Stability Tests

Stability Testing of a Composition According to the Invention

The stability of the combination product containing plabociclib tosylate and letrozole stored in an HDPE container under silica gel at 40° C. under 75% RH was tested, and both results were stable for 6 months.

| Stability-Palbociclib-Letrozole film-coated tablets | | | | | |
|---|---|---|---|---|---|
| Batch no. | AN 089 0721 | | | | |
| Strength/Pharmaceutical form | 125 mg/2.5 mg filmtablet | | | | |
| Active substance | Palbociclib-tosilate/Letrozole | | | | |
| Storage conditions | 40° C./75% RH | | | | |
| | Start | 1 hó | 2 hó | 3 hó | 6 hó |
| Water content Palbociclib | 4.29% | 2.57 | 2.59% | 2.66 | 2.69 |
| Active substance content (UPLC) [%] | 99.0 | 99.9 | 100.4 | 99.8 | 101.5 |

-continued

| Stability-Palbociclib-Letrozole film-coated tablets | | | | | |
|---|---|---|---|---|---|
| contamination (UPLC) [%] | | | | | |
| Total known contaminants | <RL | <RL | <RL | <RL | <RL |
| Total unknown contaminants [%] | <RL | <RL | <RL | <RL | <RL |
| Total contaminants [%] | <RL | <RL | <RL | <RL | <RL |
| Letrozole | | | | | |
| Active substance content (UPLC) [%] | 97.1 | 96.8 | 97.9 | 97.1 | 97.4 |
| contamination (UPLC) [%] | | | | | |
| LET IMP A | <RL | <RL | <RL | <RL | <RL |
| LET IMP B | <RL | <RL | <RL | <RL | <RL |
| Total unknown contaminants [%] | 0.20 | <RL | <RL | <RL | <RL |
| Total contaminants [%] | 0.20 | <RL | <RL | <RL | <RL |

RL: Reporting limit

The active ingredient content was measured using the HPLC method:

Equipment: Waters Acquity H-Class UPL-C system or equivalent

Column: Waters XSelect HSS PFP, 3.0×100 mm, 2.5 μm

Solvent (Diluent): 0.2% perchloric acid/Acetonitrile=50/50 (V/V %)

Eluent: A: 20 mM Ammonium acetate+0.1% perchloric acid buffer solution (pH=2.9)

B: Acetonitrile/Methanol=75/25 (V/V %)

Gradient profile:

| Time [min] | Eluent A [%] | Eluent B [%] |
|---|---|---|
| starting | 99.0 | 1.0 |
| 1.0 | 99.0 | 1.0 |
| 3.0 | 77.5 | 22.5 |
| 10.0 | 65.0 | 35.0 |
| 20.0 | 1.0 | 99.0 |
| 21.0 | 1.0 | 99.0 |
| 21.5 | 99.0 | 1.0 |
| 23.0 | 99.0 | 1.0 |

Flow rate: 0.7 mL/min

Column temperature: 26° C.

Column pressure: ~500-600 bar

Sample temperature: 20° C.

Injected sample: 2.0 μL Palbociclib; 5.0 μL Letrozole

Detection: UV, 254 nm Palbociclib; 240 nm Letrozole

Evaluation: External standard calibration method based on peak areas

Ignore limit: 0.05%

5. Compatibility Tests:

The compatibility test was performed at room temperature (25° C.), 40° C. under 75% RH and 50° C., for 1 months with the various components tested in proportion to the intended composition.

5.1. Compatibility of Letrozole-Palbociclib Tosylate Salt

No detectable decomposition products were found in the powder mixture at 25° C., 40° C. and 50° C. after one months.

5.2. Letrozole—Para-Toluenesulphonic Acid Compatibility Test

PTSA caused 5% degradation of letrozole at 25° C., 12% at 40° C. and 15% at 50° C. after 1 months, which is definitely above the limit and is already significant at room temperature.

5.3. Palbociclib Base—Para-Toluenesulphonic Acid Compatibility Test

PTSA at 25° C., 40° C. and 50° C. did not induce degradation at the palbociclib base even after one moths.

Example 6: Tablet Containing Letrozole

We proceed according to the general procedure using the WE-1 composition of embodiment 1, with the difference that palbociclib tosylate is omitted from the composition.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A pharmaceutical composition comprising the 4-toluenesulfonic acid salt of palbociclib and letrozole.

2. The pharmaceutical composition comprising the 4-toluenesulfonic acid salt of Palbociclib and letrozole according to claim 1, wherein the 4-toluenesulfonic acid salt of Palbociclib and letrozole are not isolated from each other.

3. The pharmaceutical composition comprising the 4-toluenesulfonic acid salt of Palbociclib and letrozole according to claim 1, in which the 4-toluenesulfonic acid salt of Palbociclib and letrozole are homogenized in the composition.

4. A pharmaceutical composition according to claim 1, wherein the palbociclib tosylate (1:1) is a salt form.

5. A pharmaceutical composition according to claim 4, wherein the characteristic X-ray powder diffraction peaks of the 4-toluenesulfonic acid (1:1) salt of palbociclib are as follows: Cu Kα (1.1541874 Å) (±0.2° 2θ): 5.18; 10.25; 13.45; 16.08; 21.56.

6. A pharmaceutical composition according to claim 1, comprising 10 to 50% by weight of palbocyclib tosylate salt, 0.10 to 1% by weight of letrozole;

or wherein the amount of palbociclib tosylate is 75 mg, 100 mg, or 125 mg, based on palbocyclib base, and the amount of letrozole is 2.5 mg;

or which comprises, in addition to the active ingredients, at least one further excipient, a filler, a binder, a disintegrant, a lubricant or a glidant, or a mixture thereof;

or comprising 50 to 90% by weight of diluent, optionally 1 to 10% by weight of binder, optionally 1 to 15% by weight of disintegrant and optionally 0.1-2% by weight of glidant and 0.1-3% by weight of lubricant;

or which comprises as filler an organic or inorganic filler compatible with palbociclib and letrozole, optionally, as binder a binder compatible with palbocyclib and letrozole, optionally, as a disintegrant a disintegrant compatible with palbociclib and letrozole, optionally, as lubricant a lubricant compatible with palbociclib and letrozole, optionally, as glidant a glidant compatible with palbociclib and letrozole;

or wherein the composition comprises palbociclib tosylate (1:1) salt corresponding to 75 mg, 100 mg or 125 mg of palbociclib base and 2.5 mg of letrozole, 55-85% by weight of microcrystalline cellulose, 2-10% by weight of crospovidone, 0.2-2% by weight of collidiated silica and 0.1-3.0% by weight of magnesium stearate.

7. The pharmaceutical composition according to claim 1, which is in the form of granules, comprising the 4-toluenesulfonic acid salt of palbociclib and letrozole.

8. Granules comprising the 4-toluenesulfonic acid salt of Palbociclib and letrozole, wherein the 4-toluenesulfonic acid salt of Palbociclib and letrozole are not isolated from each other;

or a compact, in which the 4-toluenesulfonic acid salt of palbociclib and letrozole have been homogenized, or 4-toluenesulfonic acid salt of palbociclib and letrozole granulated together, in which the palbociclib tosylate is in the salt form of (1:1).

9. The granules according to claim 8, in which the palbociclib tosylate (1:1) salt has characteristic X-ray powder diffraction peak positions of the following Cu Kα (1.1541874 Å) (±0.2° 2θ): 5.18; 10.25; 13.45; 16.08; 21.56.

10. The granules according to claim 8, which comprises 10-50% by weight of palbociclib tosylate salt, 0.10-1% by weight of letrozole and, optionally a filler, a binder, a disintegration aid, a lubricant or a glidant, or a mixture thereof;

or which comprise as filler an organic and/or inorganic filler compatible with palbociclib and letrozole selected from sugar alcohols and, cellulose derivatives, optionally, a binder compatible with palbociclib and letrozole, as a disintegration aid a disintegrant compatible with palbociclib and letrozole, a lubricant compatible with palbociclib and letrozole, a glidant compatible with palbociclib and letrozole.

11. A pharmaceutical composition according to claim 1, which is in a tablet, wherein the tablet is coated.

12. A process for preparing a pharmaceutical composition comprising the 4-toluenesulfonic acid salt of palbociclib and letrozole according to claim 1, which comprises homogenizing the 4-toluenesulfonic acid salt of palbociclib with the letrozole and optionally further excipients, a diluent, a disintegrant, a glidant or a lubricant, then the thus obtained homogenate is granulated by a dry granulation process, and then additional excipients, and optionally an additional disintegrant are added to the resulting granulate, and the resulting mixture is filled into capsules or tableted, wherein the tablets are optionally coated.

13. The process according to claim 12, wherein the palbocilib tosylate salt is the 4-toluenesulfonic acid (1:1) salt of palbocyclib having characteristic X-ray powder diffraction peaks: Cu Kα (1.1541874 Å) (±0.2° 2θ): 5, 18; 10.25; 13.45; 16.08; 21.56;

or wherein in the process from 10 to 50% by weight of the composition of palbocyclib tosylate salt, and from 0.10% by weight of letrozole is present;

or wherein the amount of palbocilib tosylate is 75 mg, 100 mg, or 125 mg, based on palbocyclib base, and the amount of letrozole is 2.5 mg;

or wherein 50 to 90% by weight of diluent, optionally 1 to 10% by weight of binder, optionally 1 to 15% by weight of disintegrant and optionally 0.1-2% by weight of glidant and 0.1-3% by weight of lubricant are present;

or wherein as filler an organic or inorganic filler compatible with palbociclib and letrozole is present, optionally, as binder a binder compatible with palbociclib and letrozole is present, optionally, as a disintegrant a disintegrant compatible with palbociclib and letrozole is present, optionally, as lubricant a lubricant compatible with palbociclib and letrozole is present, optionally, as glidant a glidant compatible with palbociclib and letrozole is present;

or wherein 10 to 50% by weight of the composition of the 4-toluenesulfonic acid (1:1) salt of palbociclib having a characteristic X-ray powder diffraction peak the following: Cu Kα (1.1541874 Å) (±0.2° 2θ): 5.18; 10.25; 13.45; 16.08; 21.56, 0.10-1% by weight of letrozole to 50-90% by weight of microcrystalline cellulose and optionally further excipients, 1-15% by weight of crospovidone, 0.1-2% by weight of collidiated silica and 0.1-3% by weight of magnesium stearate are mixed, the resulting mixture is homogenized, and the resulting homogenate is granulated by a dry granulation process, and then optionally further excipients, optionally 0.1-3% by weight of magnesium stearate, and optionally an additional 1-15% by weight of crospovidone are added, and then the resulting mixture is filled into a capsule or tableted and the thus obtained tablets are optionally coated.

14. A fixed-dose combination composition comprising 4-toluenesulfonic acid salt of palbociclib and letrozole according to claim 1, which is packaged in blister form, which fixed-dose preparation is a tablet or capsule.

15. A secondary packaging, which contains a blister or blisters containing a fixed-dose combination composition containing the 4-toluenesulfonic acid salt of Palbociclib and letrozole according to claim 14, and also further blister/blisters containing a mono composition containing letrozole.

16. The secondary packaging according to claim 15, in which 21 fixed-dose combination compositions containing the 4-toluenesulfonic acid salt of Palbociclib and letrozole and 7 compositions containing letrozole are placed in blisters in such a way that a.) three blisters which contain 7-7 compositions of Palbociclib 4-toluenesulfonic acid salt and a fixed-dose combination composition containing letrozole, and a fourth blister which contains 7 tablets containing letrozole, or b.) one blister which contains 21 fixed-dose combination preparations containing the 4-toluenesulfonic acid salt of Palbociclib and letrozole and another blister contains 7 tablets containing letrozole, or c.) one blister contains 14 fix dose combination compositions, another contains 7 fix dose combination compositions comprising of palbociclib 4-toluenesulfonic acid salt and letrozol and a third blister contains 7 composition containing letrozole, or d.) a blister is placed in which, from 28 unit doses, 21 are fixed-dose combination composition containing Palbociclib 4-toluenesulfonic acid salt and letrozole and 7 are mono compositions containing letrozole, which are placed in such a way that they form two separate groups in the blister;

or as above, which contains integer multiples of the blister arrangements according to points a.)-d.);

or in which, at the place of the individual unit doses, there is a marking on the blister foil and/or on cardboard on the blister foil and/or on the wallboard in the place of each unit dose, marking the time of taking the dose, or the order of taking the unit doses;

or on which the marking is a number, letter, combination of letters or numbers, a graphic sign, an arrow showing a direction, a color, a three-dimensional sign, or Braille;

or in which the drug unit doses are arranged such that each row contains 7 drug unit doses, and which rows are arranged one below the other such that 3 rows contain drug unit doses containing palbociclib 4-tosylate and letrozole, and the 4th row contains drug unit doses containing letrozole and if the package contains multiples of 28 drug unit doses, the blister contains the other drug unit doses distributed accordingly in the section consisting of 4 rows containing the next 28 tablets;

or on which numbers from 1 to 7 are displayed in each row on the blister foil or cardboard in place of each unit dose, or numbers from 1 to 28 consecutively on the blister foil or cardboard in place of each unit dose numbers are displayed in such a way that unit doses containing palbociclib 4-tosylate and letrozole are assigned numbers 1-21, while mono-unit doses containing letrozole are assigned numbers 22-28;

or in which the amount of palbociclib tosylate in the unit doses containing palbociclib 4-tosylate corresponds to 75 mg, 100 mg or 125 mg palbociclib base and the amount of letrozole is 2.5 mg.

17. The pharmaceutical preparation comprising the 4-toluenesulfonic acid salt of Palbociclib and letrozole according to claim 3, in which homogenized mixture of the 4-toluenesulfonic acid salt of Palbociclib and letrozole are granulated together.

18. The pharmaceutical composition according to claim 6, comprising 25 to 35% by weight of palbocyclib tosylate salt, 0.20 to 0.80% by weight of letrozole;

which comprises
as filler an organic or inorganic filler compatible with palbociclib and letrozole selected from sugar alcohols, mannitol, isomalt, lactitol, maltitol, sorbitol, polymeric filler, microcrystalline cellulose and silanized microcrystalline cellulose, as binder compatible with palbocyclib and letrozole selected from polyvinyl pyrrolidone, starch, dextran, cellulose derivatives, and hydroxypropyl methylcellulose, as a disintegrant compatible with palbociclib and letrozole selected from crosslinked polyvinyl pyrrolidone type disintegrant, sodium carboxyl, starch derivatives, carboxymethylcellulose salts and croscaramellose sodium, as lubricant compatible with palbociclib and letrozole selected from stearic acid, stearic acid salts, stearic acid derivatives, magnesium stearate and sodium stearyl fumarate, as glidant selected from talc, colloidal silica, anhydrous colloidal silica, and hydrophobic colloidal silica.

19. The granules according to claim 10, which comprises 25-35% by weight of palbociclib tosylate salt, 0.35-0.80% by weight of letrozole and, optionally 55-85% by weight of filler, optionally 1-10% by weight of binder, optionally 1-15% by weight of a disintegrating agent, and optionally 0.1-2% by weight glidant and 0.1-3.0% by weight of lubricant;

or which comprises
as sugar alcohol selected from mannitol, isomalt, lactitol, maltitol, and sorbitol, and as cellulose derivatives selected from microcrystalline cellulose and silanized microcrystalline cellulose, as binders compatible with palbociclib and letrozole selected from polyvinyl pyrrolidone, starch, dextran, cellulose derivatives and hydroxypropyl methyl cellulose, as disintegration aid compatible with palbociclib and letrozole selected from cross-linked polyvinyl pyrrolidone type disintegration aids, and as starch derivatives selected from sodium carboxymethyl starch, starch glycolate type A, carboxymethylcellulose salts and croscaramellose sodium, as lubricant compatible with palbociclib and letrozole stearic acid selected from stearic acid salts and stearic acid derivatives, as lubricant compatible with palbociclib and letrozole selected from talc, colloidal silicon dioxide and anhydrous colloidal silicon dioxide.

20. The secondary packaging according to claim 16, wherein the secondary package is a box or a wallet packaging.

* * * * *